(12) United States Patent
Hashimoto et al.

(10) Patent No.: US 9,747,689 B2
(45) Date of Patent: Aug. 29, 2017

(54) IMAGE PROCESSING SYSTEM, X-RAY DIAGNOSTIC APPARATUS, AND IMAGE PROCESSING METHOD

(71) Applicant: Toshiba Medical Systems Corporation, Otawara-shi (JP)

(72) Inventors: Shinichi Hashimoto, Otawara (JP); Hiroyuki Ohuchi, Otawara (JP); Takuya Sakaguchi, Utsunomiya (JP); Ko Fuchigami, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 146 days.

(21) Appl. No.: 14/663,272

(22) Filed: Mar. 19, 2015

(65) Prior Publication Data

US 2015/0193932 A1 Jul. 9, 2015

Related U.S. Application Data

(63) Continuation of application No. PCT/JP2013/075584, filed on Sep. 20, 2013.

(30) Foreign Application Priority Data

Sep. 20, 2012 (JP) ................................. 2012-207468
Sep. 20, 2013 (JP) ................................. 2013-196006

(51) Int. Cl.
*A61B 6/03* (2006.01)
*G06T 7/00* (2017.01)
(Continued)

(52) U.S. Cl.
CPC ............ *G06T 7/0024* (2013.01); *A61B 6/032* (2013.01); *A61B 6/12* (2013.01); *A61B 6/4417* (2013.01);
(Continued)

(58) Field of Classification Search
CPC ................. G06T 7/0024; G06T 7/0012; G06T 2207/10012; G06T 2207/10081;
(Continued)

(56) References Cited

U.S. PATENT DOCUMENTS 7,813,535 B2    10/2010  Florin et al.
8,805,043 B1 *   8/2014  Suri ........................ A61B 8/52
                                                                    382/131

(Continued)

FOREIGN PATENT DOCUMENTS

JP    2006-297105 A    11/2006
JP    2008-148932 A     7/2008
(Continued)

OTHER PUBLICATIONS

International Search Report mailed Dec. 24, 2013 for PCT/JP2013/075584 filed Sep. 20, 2013 with English Translation.

(Continued)

*Primary Examiner* — Amandeep Saini
(74) *Attorney, Agent, or Firm* — Oblon, McClelland, Maier & Neustadt, L.L.P.

(57) ABSTRACT

An image processing system according to an embodiment includes a first aligning unit, an output unit, a second aligning unit, and a display unit. The first aligning unit aligns first three-dimensional medical image data with second three-dimensional medical image data. The output unit outputs, as output data, data obtained by adding alignment information to the first three-dimensional medical image data and to the second three-dimensional medical image data or synthetic data obtained by aligning and synthesizing the first three-dimensional medical image data with the second three-dimensional medical image data. The second aligning unit receives the output data and aligns the second three-dimensional medical image data with one or a plurality of (Continued)

pieces of X-ray image data. The display unit displays image data obtained by aligning the first three-dimensional medical image data with X-ray image data based on an alignment result.

20 Claims, 14 Drawing Sheets

(51) Int. Cl.
*A61B 6/00* (2006.01)
*A61B 8/08* (2006.01)
*A61B 8/00* (2006.01)
*A61B 6/12* (2006.01)
*A61B 34/20* (2016.01)

(52) U.S. Cl.
CPC .............. *A61B 6/463* (2013.01); *A61B 6/466* (2013.01); *A61B 6/481* (2013.01); *A61B 6/503* (2013.01); *A61B 6/5241* (2013.01); *A61B 6/5247* (2013.01); *A61B 8/0883* (2013.01); *A61B 8/4416* (2013.01); *A61B 8/463* (2013.01); *A61B 8/466* (2013.01); *A61B 8/483* (2013.01); *A61B 8/5246* (2013.01); *A61B 8/5261* (2013.01); *G06T 7/0012* (2013.01); *A61B 6/4441* (2013.01); *A61B 2034/2048* (2016.02); *G06T 2207/10012* (2013.01); *G06T 2207/10081* (2013.01); *G06T 2207/10116* (2013.01); *G06T 2207/10121* (2013.01); *G06T 2207/10136* (2013.01); *G06T 2207/30048* (2013.01)

(58) Field of Classification Search
CPC . G06T 2207/30048; G06T 2207/10121; G06T 2207/10136; G06T 2207/10116; A61B 6/12; A61B 6/481; A61B 6/5241; A61B 8/5261; A61B 6/5247; A61B 8/0883; A61B 8/4416; A61B 8/463; A61B 8/466; A61B 8/483; A61B 8/5246; A61B 6/032; A61B 6/463; A61B 6/466; A61B 6/503; A61B 6/4417; A61B 2034/2048; A61B 6/4441

See application file for complete search history.

(56) References Cited

U.S. PATENT DOCUMENTS

| | | | |
|---|---|---|---|
| 2009/0043200 A1 | 2/2009 | Abe | |
| 2009/0281418 A1* | 11/2009 | Ruijters | A61B 6/12 600/424 |
| 2010/0231605 A1* | 9/2010 | Moriya | G06F 19/321 345/619 |
| 2010/0254583 A1 | 10/2010 | Chan et al. | |
| 2013/0028384 A1* | 1/2013 | Auvray | A61B 6/032 378/62 |

FOREIGN PATENT DOCUMENTS

| | | |
|---|---|---|
| JP | 2009-039429 A | 2/2009 |
| JP | 2009-532162 A | 9/2009 |
| JP | 2011-506033 A | 3/2011 |
| JP | 2012-050844 A | 3/2012 |

OTHER PUBLICATIONS

International Written Opinion mailed Dec. 24, 2013 for PCT/JP2013/075584 filed Sep. 20, 2013.

* cited by examiner

FIG.5
FIRST FRAME  n-TH FRAME
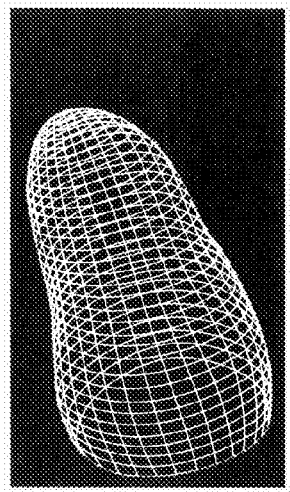 ............ 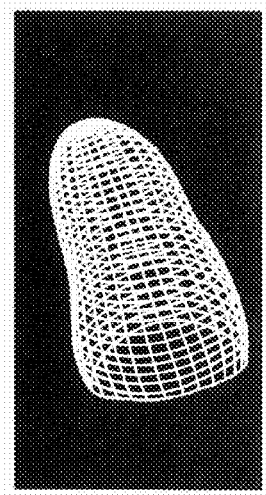
FIG.6
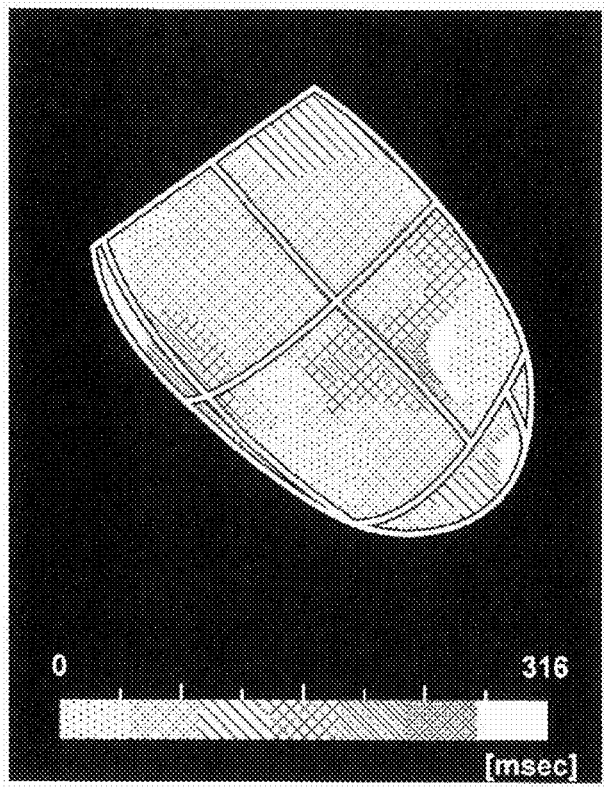

FIG.7
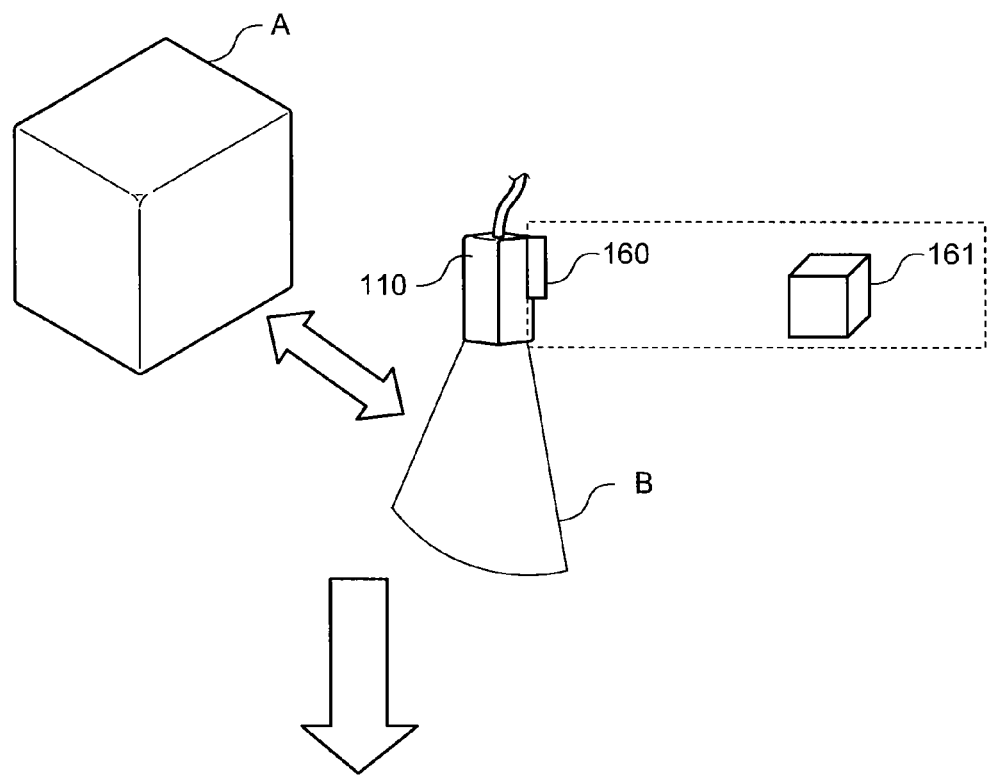
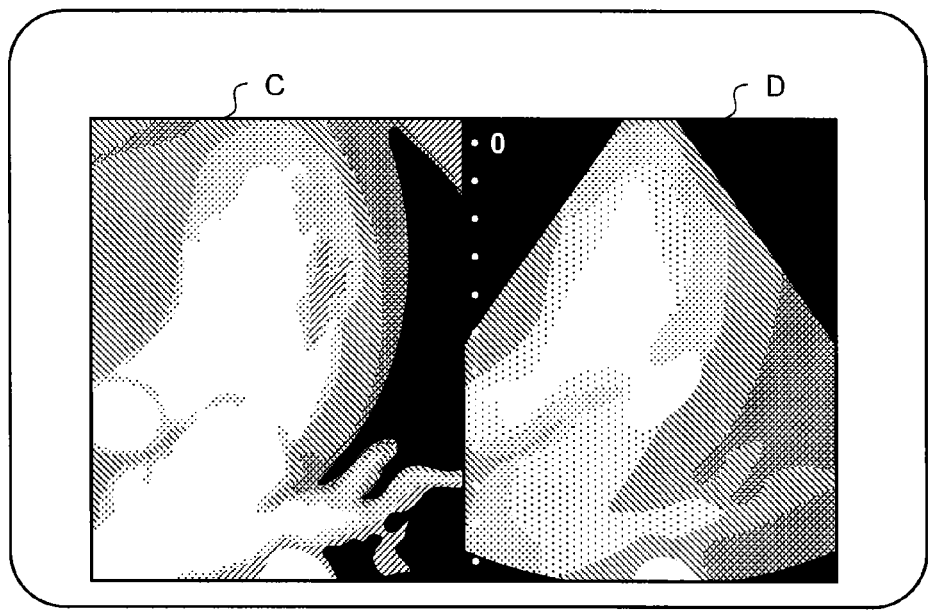

FIG.13
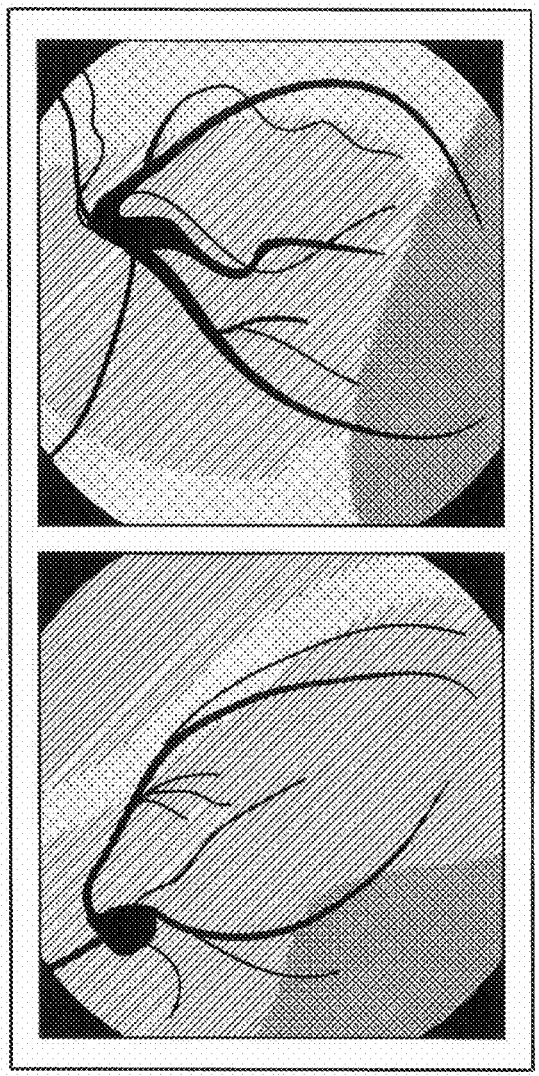
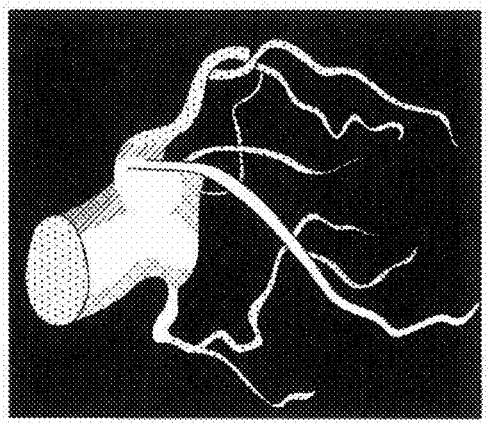

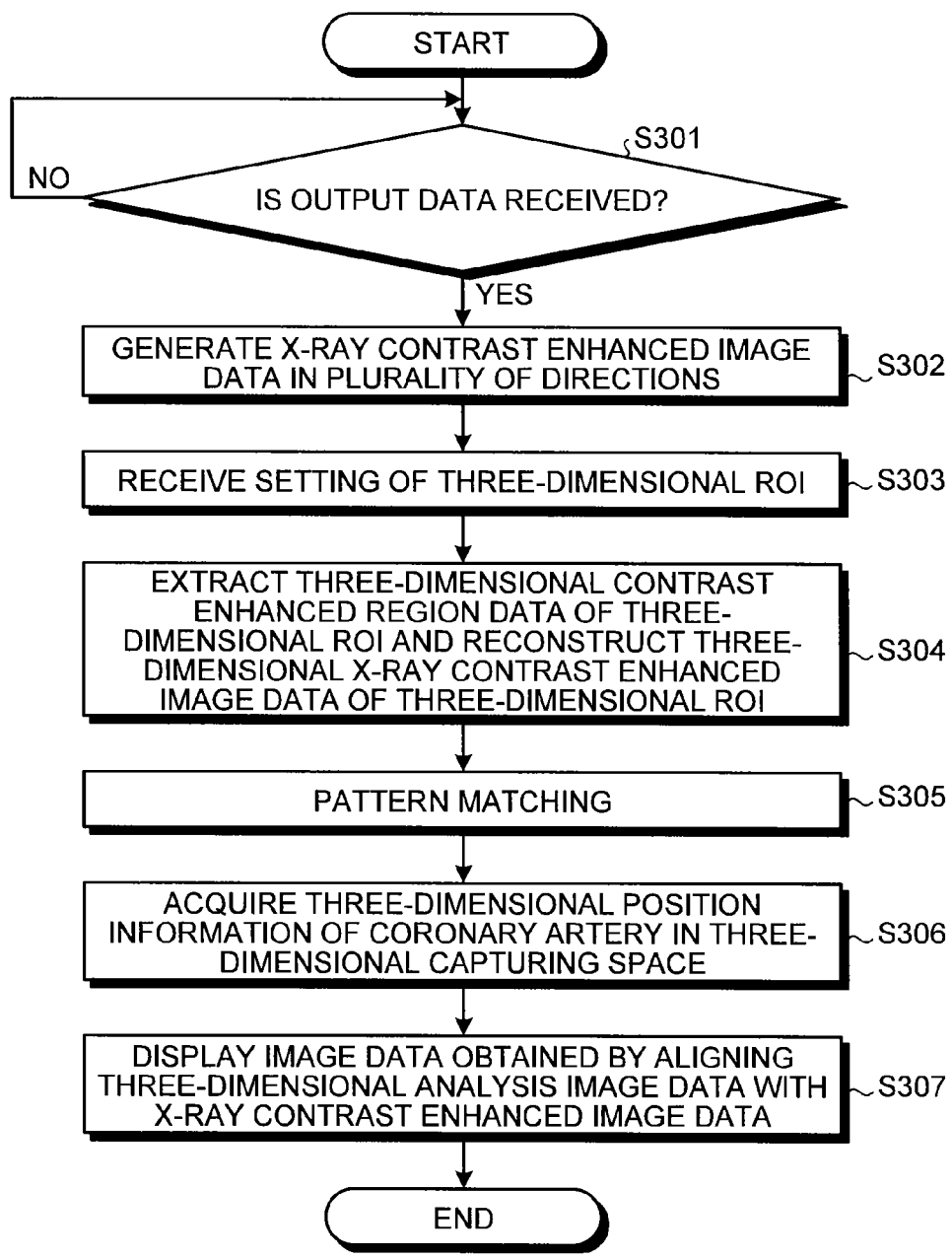

IMAGE PROCESSING SYSTEM, X-RAY DIAGNOSTIC APPARATUS, AND IMAGE PROCESSING METHOD

CROSS-REFERENCE TO RELATED APPLICATIONS

This application is a continuation of International Application No. PCT/JP2013/075584, filed on Sep. 20, 2013 which claims the benefit of priority of the prior Japanese Patent Application No. 2012-207468, filed on Sep. 20, 2012 and Japanese Patent Application No. 2013-196006, filed on Sep. 20, 2013, the entire contents of which are incorporated herein by reference.

FIELD

Embodiments described herein relate generally to an image processing system, an X-ray diagnostic apparatus, and an image processing method.

BACKGROUND

Conventionally, cardiac resynchronization therapy (CRT) is known as one of methods for treating heart failure. The CRT is a treatment method for correcting asynchrony in heart motion and restoring a pump function of the heart to nearly a normal state by placing an electrode (a pacing lead) of a pacemaker into an area at which delay in propagation of electric stimulation occurs in the heart (hereinafter, referred to as a delay area). In the CRT, a doctor places the electrode into a vein closest to the delay area while referring to an X-ray image fluoroscopically captured by an X-ray diagnostic apparatus.

Conventionally, delay areas are diagnosed using information of electrophysiology (EP), or by EP mapping in recent years, for example. In recent years, it has been known that delay areas can be diagnosed by a non-invasive analysis using an ultrasonic diagnostic apparatus. Specifically, a method for analyzing heart wall motion quantitatively by echocardiography has been in practical use in recent years. Such an analysis method can display an analysis image in which indices of local heart wall motion (e.g., strain) are mapped on an endocardium and between an endocardium and an epicardium in an ultrasound image in a color tone varying depending on the value. Because a heart is a tissue in which a myocardium is moved by mechanical excitation caused by electric stimulation, a delay area can be displayed as an area in which the heart wall motion is not synchronized (an asynchronous area) in the analysis image. The CRT treatment, however, is carried out under X-ray fluoroscopic guidance, and the analysis image is simply notified to the doctor as prior information to develop a treatment plan. Actually, it is not yet realized that the doctor is informed of a position into which the pacing lead is to be placed under the X-ray fluoroscopic guidance for the CRT treatment. On the other hand, there have been technologies for displaying an X-ray fluoroscopic image with another image superimposed thereon being developed. Since an endocardial surface and an epicardial surface of a heart wall are hard to distinguish, it is difficult to align an X-ray image with an analysis image, that is, an X-ray image with an ultrasound image.

BRIEF DESCRIPTION OF THE DRAWINGS

FIG. 3, FIG. 4, FIG. 5 and FIG. 6 are views for explaining an analyzing unit according to the first embodiment;

FIG. 7 is a view for explaining an aligning unit according to the first embodiment;

FIG. 12 and FIG. 13 are views for explaining an example of processing performed by the X-ray diagnostic apparatus according to the first embodiment;

FIG. 18 is a flowchart for explaining an example of processing performed by an X-ray diagnostic apparatus according to the second embodiment.

DETAILED DESCRIPTION

An image processing system according to an embodiment includes a first aligning unit, an output unit, a second aligning unit, and a display unit. The first aligning unit aligns first three-dimensional medical image data with second three-dimensional medical image data, the first three-dimensional medical image data and the second three-dimensional medical image data being obtained by capturing a certain tissue of a subject. The output unit outputs, as output data, data obtained by adding alignment information to the first three-dimensional medical image data and to the second three-dimensional medical image data or synthetic data obtained by aligning and synthesizing the first three-dimensional medical image data with the second three-dimensional medical image data. The second aligning unit receives the output data and aligns the second three-dimensional medical image data with one or a plurality of pieces of X-ray image data, the X-ray image data being obtained by capturing the certain tissue of the subject in one or a plurality of capturing directions, and corresponding to the respective capturing directions. The display unit displays image data obtained by aligning the first three-dimensional medical image data with the X-ray image data of the certain tissue based on an alignment result of the first aligning unit and the second aligning unit.

Exemplary embodiments of an image processing system are described below in greater detail with reference to the accompanying drawings.

First Embodiment

The following describes an exemplary configuration of an image processing system according to a first embodiment.

Figure 1:
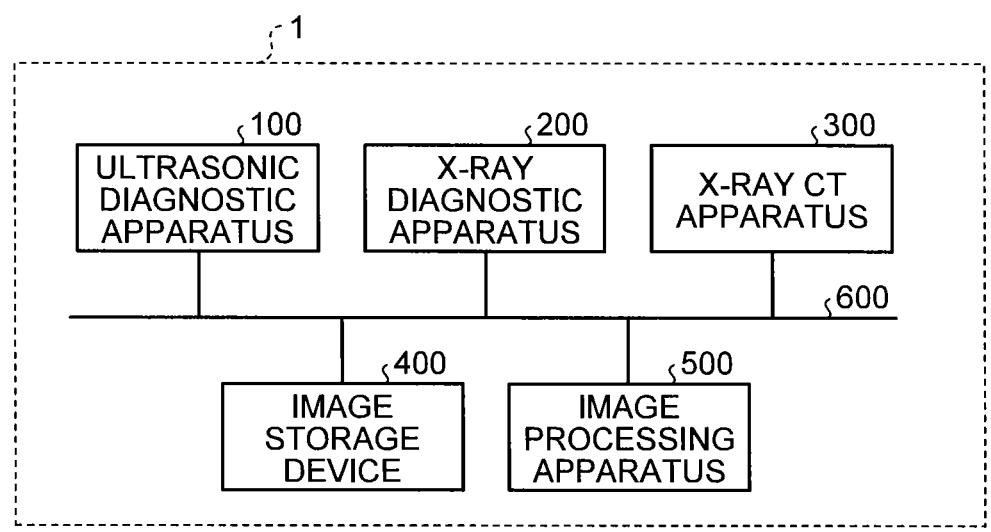
FIG. 1 is a diagram of an exemplary configuration of an image processing system according to a first embodiment.

FIG. 1 is a diagram of an exemplary configuration of the image processing system according to the first embodiment.

As illustrated in FIG. 1, an image processing system 1 according to the first embodiment includes an ultrasonic diagnostic apparatus 100, an X-ray diagnostic apparatus 200, an X-ray computed tomography (CT) apparatus 300, an image storage device 400, and an image processing apparatus 500. The apparatuses illustrated in FIG. 1 are communicable with one another directly or indirectly via an in-hospital local area network (LAN) 600 installed in a hospital, for example. In the case where a picture archiving and communication system (PACS) is introduced into a medical image diagnostic system, for example, the apparatuses transmit and receive medical images and the like to and from one another in conformity to the digital imaging and communications in medicine (DICOM).

By transmitting and receiving data conforming to the DICOM, each of the apparatuses illustrated in FIG. 1 can read and display data received from the other apparatuses. In the present embodiment, any data conforming to an arbitrary standard may be transmitted and received as long as each of the apparatuses can process the data received from the other apparatuses.

An operator adjusts the position of an ultrasound probe that performs two-dimensional ultrasonic scanning, whereby the ultrasonic diagnostic apparatus 100 generates ultrasound image data on an arbitrary section. Furthermore, the ultrasonic diagnostic apparatus 100 performs three-dimensional ultrasonic scanning with a mechanical 4D probe or a 2D array probe, thereby generating three-dimensional ultrasound image data. The X-ray diagnostic apparatus 200 performs radiography with the position of a C-arm supporting an X-ray tube and an X-ray detector fixed, thereby generating two-dimensional X-ray image data. The ultrasonic diagnostic apparatus 100 and the X-ray diagnostic apparatus 200 according to the first embodiment will be described later in detail.

The X-ray CT apparatus 300 includes a rotating frame that can rotate. The rotating frame supports an X-ray tube that irradiates a subject with an X-ray and an X-ray detector that detects the X-ray passing through the subject at positions facing each other. The X-ray CT apparatus 300 rotates the rotating frame while irradiating the subject with an X-ray output from the X-ray tube, thereby acquiring data of the X-ray subjected to transmission, absorption, and attenuation in all directions. The X-ray CT apparatus 300 reconstructs X-ray CT image data from the data thus acquired. The X-ray CT image data is a tomographic image on a rotational plane (an axial plane) of the X-ray tube and the X-ray detector. In the X-ray detector, a plurality of arrays of detection elements, which are X-ray detection elements arrayed in a channel direction, are arranged along the body axis direction of the subject. The X-ray CT apparatus 300 includes an X-ray detector in which 16 arrays of detection elements are arranged, for example. In this case, the X-ray CT apparatus 300 reconstructs a plurality of (e.g., sixteen) X-ray CT image data along the body axis direction of the subject from projection data acquired by making one full rotation of the rotating frame.

The X-ray CT apparatus 300 can reconstruct 500 pieces of X-ray CT image data including the entire heart as three-dimensional X-ray CT image data by helical scanning performed by moving a couchtop on which the subject is placed while rotating the rotating frame, for example. Alternatively, the X-ray CT apparatus 300 includes an X-ray detector in which 320 arrays of detection elements are arranged, for example. In this case, the X-ray CT apparatus 300 can reconstruct three-dimensional X-ray CT image data all-inclusively covering the entire heart simply by performing conventional scanning in which causes the rotating frame to make one full rotation. By sequentially performing the helical scanning and the conventional scanning, the X-ray CT apparatus 300 can obtain three-dimensional X-ray CT image data in a time series.

The first embodiment aligns the ultrasound image data obtained by the ultrasonic diagnostic apparatus 100 with the X-ray image data obtained by the X-ray diagnostic apparatus 200 using the three-dimensional X-ray CT image data. This will be described in detail after an explanation is made of the entire configurations of the ultrasonic diagnostic apparatus 100 and the X-ray diagnostic apparatus 200 according to the first embodiment.

The image storage device 400 is a database that stores therein medical image data. Specifically, the image storage device 400 stores and retains medical image data transmitted from the ultrasonic diagnostic apparatus 100, the X-ray diagnostic apparatus 200, and the X-ray CT apparatus 300 in a storage unit of the image storage device 400. The medical image data stored in the image storage device 400 is stored in association with accompanying information, such as a patient ID, an examination ID, an apparatus ID, and a series ID.

The image processing apparatus 500 is a workstation and a personal computer (PC) used by doctors and laboratory technicians who work for a hospital to interpret a medical image, for example. An operator of the image processing apparatus 500 performs a search using a patient ID, an examination ID, an apparatus ID, a series ID, and other IDs, thereby acquiring necessary medical image data from the image storage device 400. Alternatively, the image processing apparatus 500 may receive image data directly from the ultrasonic diagnostic apparatus 100, the X-ray diagnostic apparatus 200, and the X-ray CT apparatus 300. Besides displaying a medical image for interpretation, the image processing apparatus 500 can perform various types of image processing on medical image data.

The following describes the case where the ultrasonic diagnostic apparatus 100 and the X-ray diagnostic apparatus 200 cooperate to perform an image processing method according to the present embodiment. A part or all of various types of processing performed by the ultrasonic diagnostic apparatus 100 and the X-ray diagnostic apparatus 200 may be performed by the X-ray CT apparatus 300 and the image processing apparatus 500.

The image processing system 1 is not necessarily applied to the case where the PACS is introduced. The image processing system 1 is also applicable to the case where an electronic medical record system that manages electronic medical records accompanied with medical image data is introduced, for example. In this case, the image storage device 400 is a database that stores therein the electronic medical records. The image processing system 1 is also applicable to the case where a hospital information system (HIS) or a radiology information system (RIS) is introduced, for example.

Figure 2:
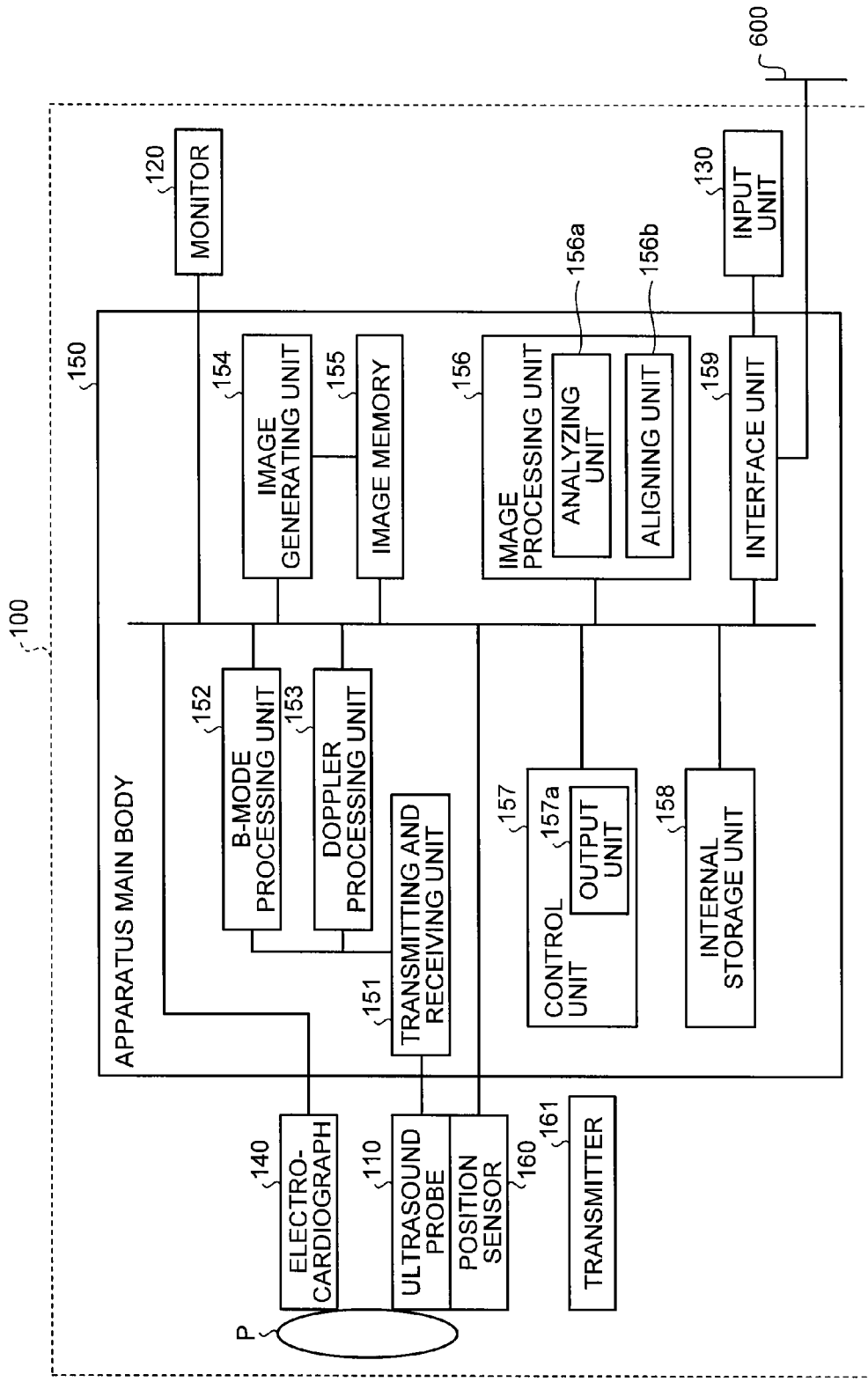
FIG. 2 is a block diagram of an exemplary configuration of an ultrasonic diagnostic apparatus according to the first embodiment.

The following describes an exemplary configuration of the ultrasonic diagnostic apparatus 100 illustrated in FIG. 1 with reference to FIG. 2. FIG. 2 is a block diagram of an exemplary configuration of the ultrasonic diagnostic apparatus according to the first embodiment. As illustrated in FIG. 1, the ultrasonic diagnostic apparatus 100 according to the first embodiment includes an ultrasound probe 110, a monitor 120, an input unit 130, an electrocardiograph 140, an apparatus main body 150, a position sensor 160, and a transmitter 161.

The ultrasound probe 110 transmits and receives ultrasonic waves. The ultrasound probe 110 includes a plurality of piezoelectric transducer elements, for example. The plurality of piezoelectric transducer elements generate ultrasonic waves based on a driving signal supplied from a transmitting and receiving unit 151 included in the apparatus main body 150, which will be described later. The ultrasound probe 110 receives reflected waves from a subject P and converts the reflected waves into an electrical signal. The ultrasound probe 110 further includes a matching layer provided to the piezoelectric transducer elements and a backing member that prevents ultrasonic waves from traveling rearward from the piezoelectric transducer elements, for example. The ultrasound probe 110 is connected to the apparatus main body 150 in an attachable and detachable manner.

If ultrasonic waves are transmitted from the ultrasound probe 110 to the subject P, the ultrasonic waves thus transmitted are sequentially reflected at an acoustic impedance discontinuous surface in a body tissue of the subject P. The ultrasonic waves are received by the plurality of piezoelectric transduce elements included in the ultrasound probe 110 as a reflected wave signal. The amplitude of the reflected wave signal thus received depends on difference in the acoustic impedance on the discontinuous surface on which the ultrasonic waves are reflected. A reflected wave signal obtained when the ultrasonic pulse thus transmitted is reflected by a moving bloodstream, the surface of a heart wall, or the like depends on a velocity component of the moving object with respect to an ultrasonic-wave transmitting direction because of the Doppler effect, thereby undergoing frequency shift.

The ultrasound probe 110 according to the first embodiment is an ultrasound probe that can scan the subject P two-dimensionally and scan the subject P three-dimensionally with ultrasonic waves. Specifically, the ultrasound probe 110 according to the first embodiment is a mechanical 4D probe that scans the subject P two-dimensionally using the plurality of piezoelectric transduce elements arranged in a line and scans the subject P three-dimensionally by oscillating the plurality of piezoelectric transduce elements at a predetermined angle (an oscillation angle). Alternatively, the ultrasound probe 110 according to the first embodiment is a 2D array probe that can perform ultrasonic scanning on the subject P three-dimensionally with the plurality of piezoelectric transduce elements arranged in a matrix. The 2D array probe can also scan the subject P two-dimensionally by focusing and transmitting the ultrasonic waves.

The input unit 130 includes a mouse, a keyboard, a button, a panel switch, a touch command screen, a foot switch, a trackball, and a joystick, for example. The input unit 130 receives various types of setting requests from an operator of the ultrasonic diagnostic apparatus 100 and transfers the various types of setting requests thus received to the apparatus main body 150.

The monitor 120 displays a graphical user interface (GUI) through which the operator of the ultrasonic diagnostic apparatus 100 inputs various types of setting request with the input unit 130 and displays ultrasound image data generated in the apparatus main body 150, for example.

The electrocardiograph 140 acquires an electrocardiogram (ECG) of the subject P as a biomedical signal of the subject P. The electrocardiograph 140 transmits the ECG thus acquired to the apparatus main body 150.

The position sensor 160 and the transmitter 161 are devices that acquire the position information of the ultrasound probe 110. The position sensor 160 is a magnetic sensor attached to the ultrasound probe 110, for example. The transmitter 161 is arranged at an arbitrary position and generates a magnetic field extending outward from the transmitter 161 with the transmitter 161 being the center.

The position sensor 160 detects the three-dimensional magnetic field generated by the transmitter 161. The position sensor 160 derives the position (coordinates and an angle) of the position sensor 160 in a space with its origin at the transmitter 161 based on the information of the magnetic field thus detected and transmits the position thus derived to the apparatus main body 150. The position sensor 160 transmits the three-dimensional coordinates and angle at which the position sensor 160 is positioned to the apparatus main body 150 as the three-dimensional position information of the ultrasound probe 110.

The present embodiment is also applicable to the case where the position information of the ultrasound probe 110 is acquired by a system other than the position detecting system using the position sensor 160 and the transmitter 161. The present embodiment may acquire the position information of the ultrasound probe 110 using a gyro sensor and an acceleration sensor, for example.

The apparatus main body 150 is a device that generates ultrasound image data based on a reflected wave signal received by the ultrasound probe 110. The apparatus main body 150 illustrated in FIG. 2 is a device that can generate two-dimensional ultrasound image data based on two-dimensional reflected wave data received by the ultrasound probe 110. Furthermore, the apparatus main body 150 illustrated in FIG. 1 is a device that can generate three-dimensional ultrasound image data based on three-dimensional reflected wave data received by the ultrasound probe 110.

As illustrated in FIG. 2, the apparatus main body 150 includes the transmitting and receiving unit 151, a B-mode processing unit 152, a Doppler processing unit 153, an image generating unit 154, an image memory 155, an image processing unit 156, a control unit 157, an internal storage unit 158, and an interface unit 159.

The transmitting and receiving unit 151 includes a pulse generator, a transmission delay unit, a pulser, and other components, and supplies a driving signal to the ultrasound probe 110. The pulse generator repeatedly generates a rate pulse that forms transmission ultrasonic waves at a predetermined rate frequency. The transmission delay unit supplies delay times required for the respective piezoelectric transducer elements to focus ultrasonic waves generated from the ultrasound probe 110 into a beam and to determine the transmission directivity to the respective rate pulses generated by the pulse generator. The pulser applies a driving signal (a driving pulse) to the ultrasound probe 110 at a timing based on the rate pulse. Specifically, the transmission delay unit changes the delay times supplied to the respective rate pulses, thereby arbitrarily controlling the direction of transmission of the ultrasonic waves transmitted from the piezoelectric transducer element surface.

The transmitting and receiving unit 151 has a function to instantaneously change a transmission frequency, a transmission driving voltage, and other elements so as to perform a predetermined scanning sequence based on an instruction issued from the control unit 157, which will be described later. Specifically, the transmission driving voltage is changed by a linear-amplifier oscillating circuit that can instantaneously change the value of the transmission driving voltage or a mechanism that electrically switches a plurality of power-supply units.

The transmitting and receiving unit 151 further includes a pre-amplifier, an analog/digital (A/D) converter, a reception delay unit, and an adder, for example. The transmitting and receiving unit 151 performs various types of processing on a reflected wave signal received by the ultrasound probe 110, thereby generating reflected wave data. The pre-amplifier amplifies a reflected wave signal on each channel. The A/D converter performs A/D conversion on the reflected wave signal thus amplified. The reception delay unit supplies a delay time required to determine the reception directivity. The adder performs addition on the reflected wave signal processed by the reception delay unit, thereby generating reflected wave data. The addition performed by the adder emphasizes a reflection component in a direction corresponding to the reception directivity of the reflected wave signal. Based on the reception directivity and the transmission directivity, a synthetic beam for transmitting and receiving ultrasonic waves is formed.

To scan the subject P two-dimensionally, the transmitting and receiving unit 151 causes the ultrasound probe 110 to transmit a two-dimensional ultrasonic beam. The transmitting and receiving unit 151 generates two-dimensional reflected wave data from a two-dimensional reflected wave signal received by the ultrasound probe 110. To scan the subject P three-dimensionally, the transmitting and receiving unit 151 causes the ultrasound probe 110 to transmit a three-dimensional ultrasonic beam. The transmitting and receiving unit 151 generates three-dimensional reflected wave data from a three-dimensional reflected wave signal received by the ultrasound probe 110.

An output signal from the transmitting and receiving unit 151 may have various forms being selectable, including a signal containing phase information, which is called a radio frequency (RF) signal, and amplitude information obtained after envelope detection is performed, for example.

The B-mode processing unit 152 receives reflected wave data from the transmitting and receiving unit 151. The B-mode processing unit 152 performs logarithmic amplification, envelope detection, and other processing on the reflected wave data, thereby generating data (B-mode data) representing the signal intensity by the intensity of brightness.

The Doppler processing unit 153 performs a frequency analysis on velocity information in the reflected wave data received from the transmitting and receiving unit 151. The Doppler processing unit 153 extracts a bloodstream, a tissue, and a contrast medium echo component by the Doppler effect and generates data (Doppler data) by extracting moving object information, such as velocity, dispersion, and power, at multiple points.

The B-mode processing unit 152 and the Doppler processing unit 153 according to the first embodiment can process both two-dimensional reflected wave data and three-dimensional reflected wave data. In other words, the B-mode processing unit 152 generates two-dimensional B-mode data from two-dimensional reflected wave data and generates three-dimensional B-mode data from three-dimensional reflected wave data. The Doppler processing unit 153 generates two-dimensional Doppler data from two-dimensional reflected wave data and generates three-dimensional Doppler data from three-dimensional reflected wave data.

The image generating unit 154 generates ultrasound image data from the data generated by the B-mode processing unit 152 and the Doppler processing unit 153. In other words, the image generating unit 154 generates two-dimensional B-mode image data representing the intensity of reflected waves by the brightness from the two-dimensional B-mode data generated by the B-mode processing unit 152. Furthermore, the image generating unit 154 generates two-dimensional Doppler image data indicating the moving object information from the two-dimensional Doppler data generated by the Doppler processing unit 153. The two-dimensional Doppler image data is a velocity image, a dispersion image, a power image, or a combination image of these images.

Typically, the image generating unit 154 converts (scan-converts) a scanning-line signal row in ultrasonic scanning into a scanning-line signal row in a video format as exemplified by television and the like, thereby generating ultrasound image data for display. Specifically, the image generating unit 154 performs coordinate transformation based on the form of the ultrasonic scanning performed by the ultrasound probe 110, thereby generating the ultrasound image data for display. The image generating unit 154 performs various types of image processing besides the scan-conversion on a plurality of image frames thus scan-converted. Examples of the various types of image processing include image processing for regenerating a brightness average value image (smoothing processing) and image processing using a differential filter in an image (edge emphasizing processing). The image generating unit 154 synthesizes character information of various types of parameters, a scale, and a body mark on the ultrasound image data, for example.

In other words, the B-mode data and the Doppler data are ultrasound image data before the scan-conversion. The data generated by the image generating unit 154 is ultrasound image data for display after the scan-conversion. The B-mode data and the Doppler data are also referred to as raw data.

The image generating unit 154 performs coordinate transformation on the three-dimensional B-mode data generated by the B-mode processing unit 152, thereby generating three-dimensional B-mode image data. Furthermore, the image generating unit 154 performs coordinate transformation on the three-dimensional Doppler data generated by the Doppler processing unit 153, thereby generating three-dimensional Doppler image data. In other words, the image generating unit 154 generates "three-dimensional B-mode image data and three-dimensional Doppler image data" as "three-dimensional ultrasound image data".

To generate various types of two-dimensional image data for displaying three-dimensional ultrasound image data (volume data) on the monitor 120, the image generating unit 154 performs rendering on the volume data. Examples of the rendering performed by the image generating unit 154 include processing for generating multi-planar reconstruction (MPR) image data from volume data by performing MPR. Examples of the rendering performed by the image generating unit 154 further include processing for performing "curved MPR" on volume data and processing for performing "maximum intensity projection" on volume data. Examples of the rendering performed by the image generating unit 154 further include volume rendering (VR) for generating two-dimensional image data reflecting three-dimensional information.

The image memory 155 is a memory that stores therein image data for display generated by the image generating unit 154. The image memory 155 can also store therein data generated by the B-mode processing unit 152 and the Doppler processing unit 153. The B-mode data and the Doppler data stored in the image memory 155 can be retrieved by the operator after a diagnosis, for example, and are converted into ultrasound image data for display via the image generating unit 154. The image generating unit 154 stores ultrasound image data and a time of ultrasonic scanning performed to generate the ultrasound image data in the image memory 155 in association with an ECG transmitted from the electrocardiograph 140. An analyzing unit 156a and the control unit 157, which will be described later, refer to the data stored in the image memory 155, thereby acquiring a cardiac time phase in the ultrasonic scanning performed to generate the ultrasound image data.

The internal storage unit 158 stores therein various types of data, such as a control program for performing transmission and reception of ultrasonic waves, image processing, and display processing, diagnosis information (e.g., a patient ID and findings of a doctor), a diagnosis protocol, and various types of body marks. Furthermore, the internal storage unit 158 is used to retain image data stored in the image memory 155 as needed, for example. The data stored in the internal storage unit 158 can be transferred to external apparatuses via the interface unit 159, which will be described later. Data stored in the external apparatuses can be transferred to the internal storage unit 158 via the interface unit 159, which will be described later. The external apparatuses correspond to the X-ray diagnostic apparatus 200, the X-ray CT apparatus 300, the image storage device 400, and the image processing apparatus 500 illustrated in FIG. 1, for example.

The image processing unit 156 is provided to the apparatus main body 150 to perform a computer-aided diagnosis (CAD). The image processing unit 156 acquires ultrasound image data stored in the image memory 155 and performs an image analysis thereon. The image processing unit 156 stores the analysis result in the image memory 155 and the internal storage unit 158.

As illustrated in FIG. 2, the image processing unit 156 includes the analyzing unit 156a and an aligning unit 156b. The analyzing unit 156a analyzes a time-series three-dimensional ultrasound image data group generated by performing three-dimensional ultrasonic scanning on the subject P, thereby generating three-dimensional analysis image data relating to local motion in a certain tissue.

The certain tissue corresponds to a heart, and the analyzing unit 156a generates information relating to motion in each region of the heart wall. The analyzing unit 156a generates analysis image data in which heart wall motion information is mapped on the endocardium and between the endocardium and the epicardium in the ultrasound image data. The analyzing unit 156a according to the first embodiment uses the three-dimensional ultrasound image data group, thereby generating three-dimensional time-series data of the heart wall motion information.

The following describes the analysis performed by the analyzing unit 156a according to the first embodiment with reference to FIG. 3 to FIG. 6. FIG. 3 to FIG. 6 are views for explaining the analyzing unit according to the first embodiment.

The operator uses the ultrasound probe 110 that can perform three-dimensional scanning, thereby performing three-dimensional scanning on the left side of the heart of the subject P by apical approach for a time period equal to or longer than one heartbeat, for example. As a result, the image generating unit 154 generates a plurality of pieces of time-series three-dimensional ultrasound image data in a time period equal to or longer than one heartbeat and stores the plurality of pieces of three-dimensional ultrasound image data in the image memory 155. The plurality of pieces of three-dimensional ultrasound image data stored in the image memory 155 are a three-dimensional ultrasound image data group generated by performing ultrasonic scanning on the heart including at least the left ventricle for a time period equal to or longer than one heartbeat. The three-dimensional ultrasound image data group is a three-dimensional B-mode image data group.

Figure 3:
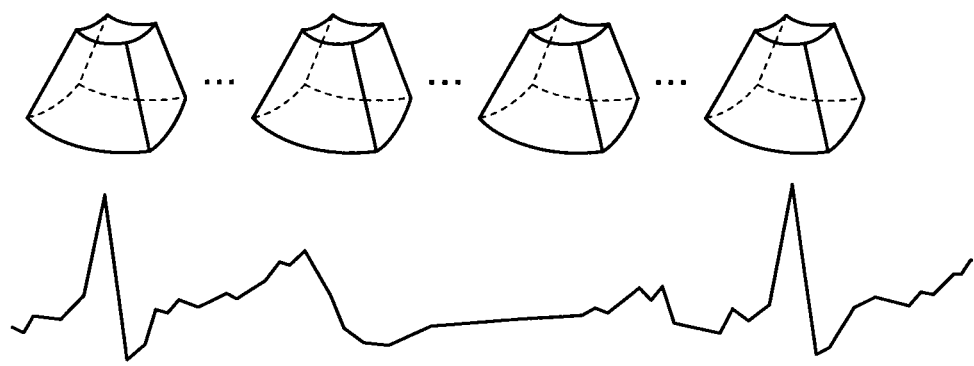

As illustrated in FIG. 3, the analyzing unit 156a acquires the plurality of pieces of time-series three-dimensional ultrasound image data in a time period equal to or longer than one heartbeat. Each of the plurality of pieces of three-dimensional ultrasound image data includes the left ventricle of the subject P.

The analyzing unit 156a derives time-series data of the heart wall motion information in the left ventricle from the three-dimensional ultrasound image data group. Specifically, the analyzing unit 156a uses the result of tracking of tracking points described below performed by processing including pattern matching between a plurality of pieces of image data, thereby deriving the heart wall motion information. More specifically, the analyzing unit 156a uses the result of 3D speckle tracking (hereinafter, referred to as "3DT") performed on three-dimensional moving image data obtained by a three-dimensional echocardiography method, thereby deriving the heart wall motion information. The speckle tracking method is a method for estimating accurate motion by performing the pattern matching in combination with an optical flow method and various types of spatiotemporal interpolation, for example. Some speckle tracking methods estimate the motion without performing the pattern matching.

The input unit 130, for example, receives a display request of the first frame (first volume) of the three-dimensional ultrasound image data group from the operator. The control unit 157 to which the display request is transferred reads three-dimensional ultrasound image data of the first frame from the image memory 155 and displays the three-dimensional ultrasound image data on the monitor 120. The control unit 157, for example, causes the image generating unit 154 to generate a plurality of pieces of MPR image data by cutting the three-dimensional ultrasound image data of the first frame on sections in a plurality of directions and to display the plurality of pieces of MPR image data on the monitor 120. The monitor 120 displays the plurality of pieces of MPR image data as illustrated in FIG. 4, for example.

Figure 4:
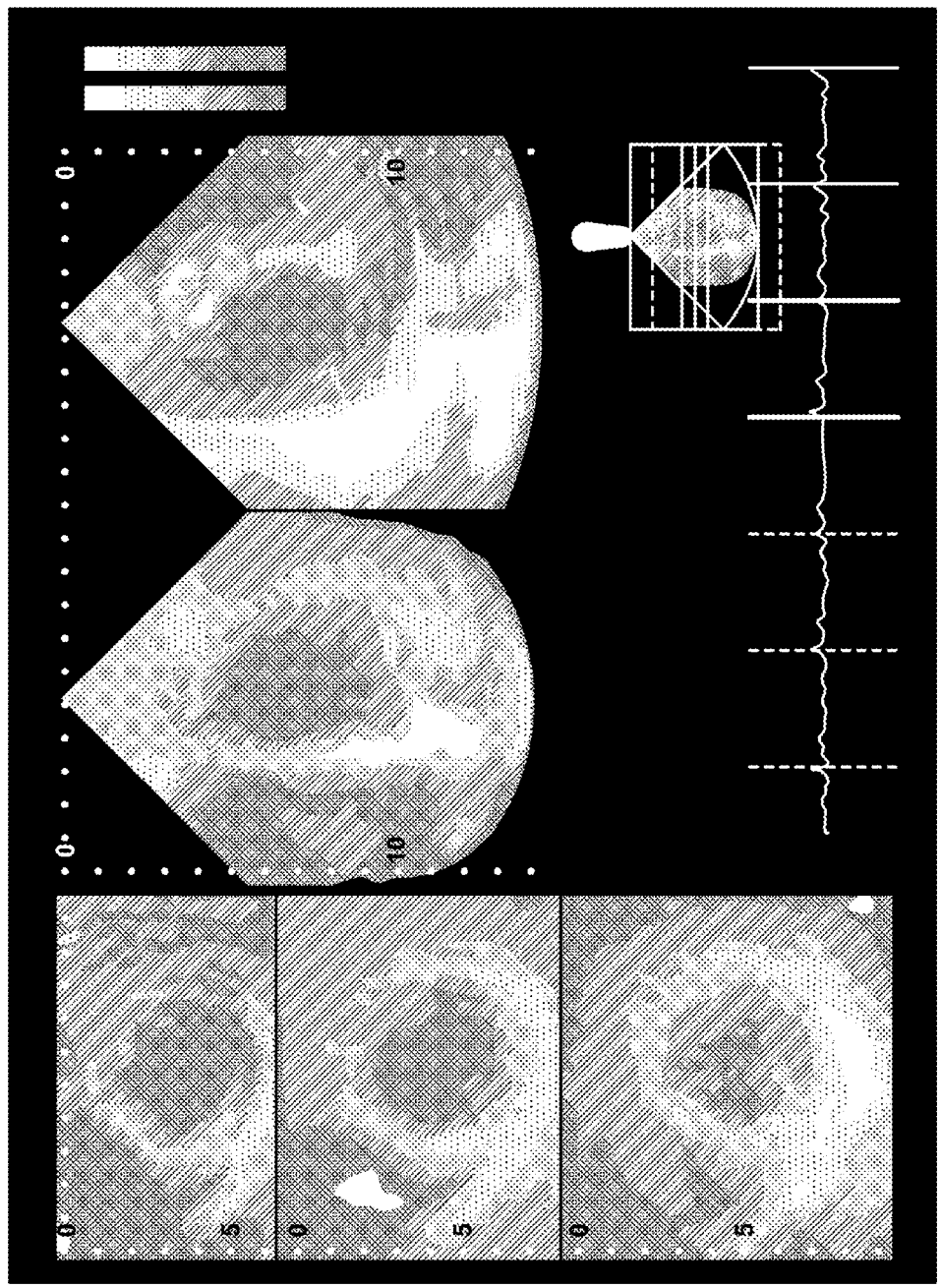

In the example of FIG. 4, the monitor 120 displays MPR image data of a plane A in an area A. In the example of FIG. 4, the monitor 120 displays MPR image data of a plane B in an area B. In the example of FIG. 4, the monitor 120 displays MPR image data of a plane C of a C3 level closer to the cardiac apex in an area C3. In the example of FIG. 4, the monitor 120 displays MPR image data of the plane C of a C7 level closer to the cardiac base in the area C7. In the example of FIG. 4, the monitor 120 displays MPR image data of the plane C of a C5 level intermediate between the cardiac apex and the cardiac base in an area C5. In the example of FIG. 4, the area C3, the area C5, and an area C7 are arranged in descending order in the left display area. The area A is arranged on the right side of the area C3 and the area C5, and the area B is arranged on the right side of the area A.

In the example of FIG. 4, the monitor 120 displays a volume rendering image of the three-dimensional ultrasound image data of the first frame and the ECG in the lower right area of the screen.

The operator refers to the plurality of pieces of MPR image data displayed on the monitor 120, thereby setting a plurality of tracking points used for performing 3DT. The operator, for example, traces the positions of the endocardium of the left ventricle and the epicardium in each piece of MPR image data, thereby specifying the endocardial outline and the epicardial outline. The analyzing unit 156a forms a three-dimensional endocardial outline and a three-dimensional epicardial outline from the endocardial outline and the epicardial outline thus specified. The analyzing unit 156a sets the points forming the three-dimensional endocardial outline in the first frame as tracking points as illustrated in FIG. 5. The analyzing unit 156a also sets the points forming the three-dimensional epicardial outline in the first frame as tracking points, which is not illustrated. The analyzing unit 156a sets template data to each of the plurality of tracking points set in the first frame. The template data is formed of a plurality of voxels around each tacking point.

The analyzing unit 156a searches for an area that matches best to the speckle pattern of the template data between two frames, thereby tracking the template data to find out to which position the template data moves in the next frame. Thus, the analyzing unit 156a tracks each of the tracking points in the first frame to find out to which positions in the n-th frame the tracking points in the first frame move as illustrated in FIG. 5. The mesh used for setting the tracking points may be set by the analyzing unit 156a detecting the endocardial surface and the epicardial surface of the left ventricle included in the first frame.

The analyzing unit 156a performs 3DT on the three-dimensional ultrasound image data group for the entire left ventricle (e.g., the endocardium of the left ventricle and the epicardium of the left ventricle). Based on the result of the 3DT performed on the three-dimensional ultrasound image data group, the analyzing unit 156a generates time-series data of the heart wall motion information on each tracking point. The analyzing unit 156a derives strain as the heart wall motion information from the result of the 3DT of the endocardium and the epicardium, for example. The analyzing unit 156a derives strain in the longitudinal direction (LS), strain in the circumferential direction (CS), and strain in the radial direction (RS).

Alternatively, the analyzing unit 156a derives the area change ratio (AC) of the endocardial surface of the left ventricle as the heart wall motion information from the result of the 3DT of the endocardium, for example. Still alternatively, the analyzing unit 156a may derive displacement from the result of the 3DT of the endocardium or the epicardium, for example. In the case where the displacement is employed as the heart wall motion information, the analyzing unit 156a can derive displacement in the longitudinal direction (LD) and displacement in the radial direction (RD). Alternatively, the analyzing unit 156a may derive absolute displacement (AD) of the tracking points at a time phase other than a reference phase with respect to the positions of the respective tracking points at a reference time phase (e.g., an R-wave). Still alternatively, to grasp the asynchrony in the motion of the heart, the analyzing unit 156a may derive an analysis result of mapping of time when the strain value is equal to or larger than a certain value or an analysis result of mapping of time when the strain value reaches the maximum.

The analyzing unit 156a may generate the time-series data of the heart wall motion information for each tracking point or for each local region. The analyzing unit 156a derives local heart wall motion information using a segmented region of 16 or 17 segments, which is recommended by the American Society of Echocardiography (ASE) and the American Heart Association (AHA), for example. Examples of the segments recommended by the ASE include an anterior wall septum (ant-sept.), an anterior wall (ant.), a lateral wall (lat.), a posterior wall (post.), an inferior wall (inf.), and a septum (sept.)

The analyzing unit 156a converts the values of the heart wall motion information obtained at the respective tracking points into color scales and maps the values onto a surface rendering image of the three-dimensional endocardial outline, thereby generating three-dimensional analysis image data as illustrated in FIG. 6, for example. The operator can observe the three-dimensional analysis image data illustrated in FIG. 6 on the monitor 120 in various directions by moving the viewpoint position. Alternatively, the analyzing unit 156a converts the values of the heart wall motion information obtained at the respective tracking points into color scales and maps the values onto a polar-map of 16 segments, thereby generating three-dimensional analysis image data, for example.

Referring back to FIG. 2, the aligning unit 156b aligns ultrasound image data with a second type of three-dimensional medical image data. The second type of three-dimensional medical image data corresponds to three-dimensional X-ray CT image data received from the X-ray CT apparatus 300, for example. Alternatively, the second type of three-dimensional medical image data corresponds to three-dimensional MRI image data received from a magnetic resonance imaging (MRI) apparatus, which is not illustrated in FIG. 1, for example. The ultrasonic diagnostic apparatus 100 according to the first embodiment can cause the image generating unit 154 to generate medical image data on nearly the same section as the section of two-dimensional ultrasonic scanning performed to generate two-dimensional ultrasound image data by processing of the position sensor 160 and the aligning unit 156b and displays the medical image data on the monitor 120.

Before performing echocardiography of the subject P with the ultrasound probe 110, for example, the operator requests transmission of three-dimensional X-ray CT image data obtained by capturing the heart of the subject P. Furthermore, the operator adjusts the position of the section for MPR processing via the input unit 130 such that two-dimensional X-ray CT image data depicting the examination area of the subject P is displayed on the monitor 120.

Under the control of the aligning unit 156b, the image generating unit 154 generates two-dimensional X-ray CT image data obtained by cutting the three-dimensional X-ray CT image data on the section (hereinafter, referred to as an initial section) adjusted by the operator. The monitor 120 displays the two-dimensional X-ray CT image data generated by the image generating unit 154. The operator operates the ultrasound probe 110 so as to perform ultrasonic scanning on the same section as that of the X-ray CT image data displayed on the monitor 120. If it is determined that the sections of the two-dimensional X-ray CT image data and the two-dimensional ultrasound image data displayed on the monitor 120 are nearly the same, the operator specifies three corresponding points on both image data, for example. Alternatively, the operator specifies one or more corresponding points and axes (lines) on both image data, for example. The operator then presses a confirmation button of the input unit 130. The aligning unit 156b sets three-dimensional position information of the ultrasound probe 110 acquired from the position sensor 160 when the confirmation button is pressed as initial position information. The aligning unit 156b aligns the coordinate system of the two-dimensional ultrasound image data with the coordinate system of the three-dimensional X-ray CT image data using the points or the lines corresponding to each other. FIG. 7 is a view for explaining the aligning unit according to the first embodiment.

Subsequently, the aligning unit 156b acquires the three-dimensional position information of the ultrasound probe 110 when generating two-dimensional ultrasound image data B illustrated in FIG. 7 from the position detecting system formed of the position sensor 160 and the transmitter 161. The aligning unit 156b acquires movement information between the three-dimensional position information thus acquired and the initial position information. Based on the movement information thus acquired, the aligning unit 156b changes the position of the initial section, thereby resetting the section for MPR. Under the control of the aligning unit 156b, the image generating unit 154 generates two-dimensional X-ray CT image data C from three-dimensional X-ray CT image data A illustrated in FIG. 7 on the section reset by the aligning unit 156b. Under the control of the aligning unit 156b, the monitor 120 displays the two-dimensional X-ray CT image data C and the two-dimensional ultrasound image data B in parallel as illustrated in FIG. 7. The explanation has been made of the case where alignment is performed using the position sensor 160. Alignment of the three-dimensional ultrasound image data with the three-dimensional X-ray CT image data (or three-dimensional MRI image data), however, can be performed as well without using the position sensor 160, by specifying three or more common feature points on both image data after acquiring the three-dimensional ultrasound image data. For example, if displaying both MPR image data, setting the common features individually, synchronizing the images at a time when more than three-points have been set, then a similar concurrent display as using the position sensor 160 by an interface such as a mouse, becomes possible.

The concurrent display function enables the operator to simultaneously observe an ultrasound image and an X-ray CT image on nearly the same section as that of the ultrasound image, for example. By performing two-dimensional scanning with the ultrasound probe 110 that can perform three-dimensional scanning and by acquiring the initial position information and the position information of the points and the lines in correspondence, the aligning unit 156b can identify nearly the same three-dimensional region as that on which three-dimensional ultrasonic scanning is performed in the three-dimensional X-ray CT image data. The aligning unit 156b can also align voxels constituting the three-dimensional ultrasound image data with respective voxels constituting the three-dimensional X-ray CT image data.

In other words, the aligning unit 156b can align three-dimensional ultrasound image data with three-dimensional X-ray CT image data and align three-dimensional ultrasound image data with three-dimensional MRI image data. Furthermore, the aligning unit 156b can align three-dimensional analysis image data with three-dimensional X-ray CT image data using alignment information of the three-dimensional ultrasound image data and the three-dimensional X-ray CT image data. Similarly, the aligning unit 156b can align three-dimensional analysis image data with three-dimensional MRI image data using alignment information of the three-dimensional ultrasound image data and the three-dimensional MRI image data. In the case where the three-dimensional X-ray CT image data and the three-dimensional MRI image data are three-dimensional contrast enhanced image data obtained by contrast enhanced radiography, the aligning unit 156b can align three-dimensional contrast enhanced region data segmented from the three-dimensional contrast enhanced image data with three-dimensional analysis image data.

Referring back to FIG. 2, the control unit 157 controls the entire processing of the ultrasonic diagnostic apparatus 100. Specifically, the control unit 157 controls the processing of the transmitting and receiving unit 151, the B-mode processing unit 152, the Doppler processing unit 153, the image generating unit 154, and the analyzing unit 156a based on various types of setting requests received from the operator via the input unit 130 and various types of control programs and various types of data read from the internal storage unit 158. The control unit 157 performs control such that the monitor 120 displays ultrasound image data for display stored in the image memory 155 and the internal storage unit 158. Furthermore, the control unit 157 performs control such that the monitor 120 displays the processing result of the analyzing unit 156a.

The control unit 157 outputs the processing result of the analyzing unit 156a and other data to the external apparatuses via the interface unit 159, which will be described later. The external apparatuses correspond to the X-ray diagnostic apparatus 200, the X-ray CT apparatus 300, the image storage device 400, and the image processing apparatus 500 illustrated in FIG. 1, for example. The control unit 157 according to the first embodiment includes an output unit 157a illustrated in FIG. 2 serving as a processing unit that outputs output data and controls the data format of the output data. The processing performed by the output unit 157a will be described later in detail.

The interface unit 159 is an interface provided for the input unit 130, an in-hospital LAN 600, the X-ray diagnostic apparatus 200, the X-ray CT apparatus 300, the image storage device 400, and the image processing apparatus 500. Various types of setting information and various types of instructions received from the operator by the input unit 130 are transferred to the control unit 157 by the interface unit 159, for example. Output data output from the output unit 157a is transmitted to the X-ray diagnostic apparatus 200 by the interface unit 159 via the in-hospital LAN 600, for example. Data including three-dimensional medical image data transmitted from the X-ray CT apparatus 300 and the image storage device 400 is stored in the internal storage unit 158 via the interface unit 159, for example.

Figure 8:
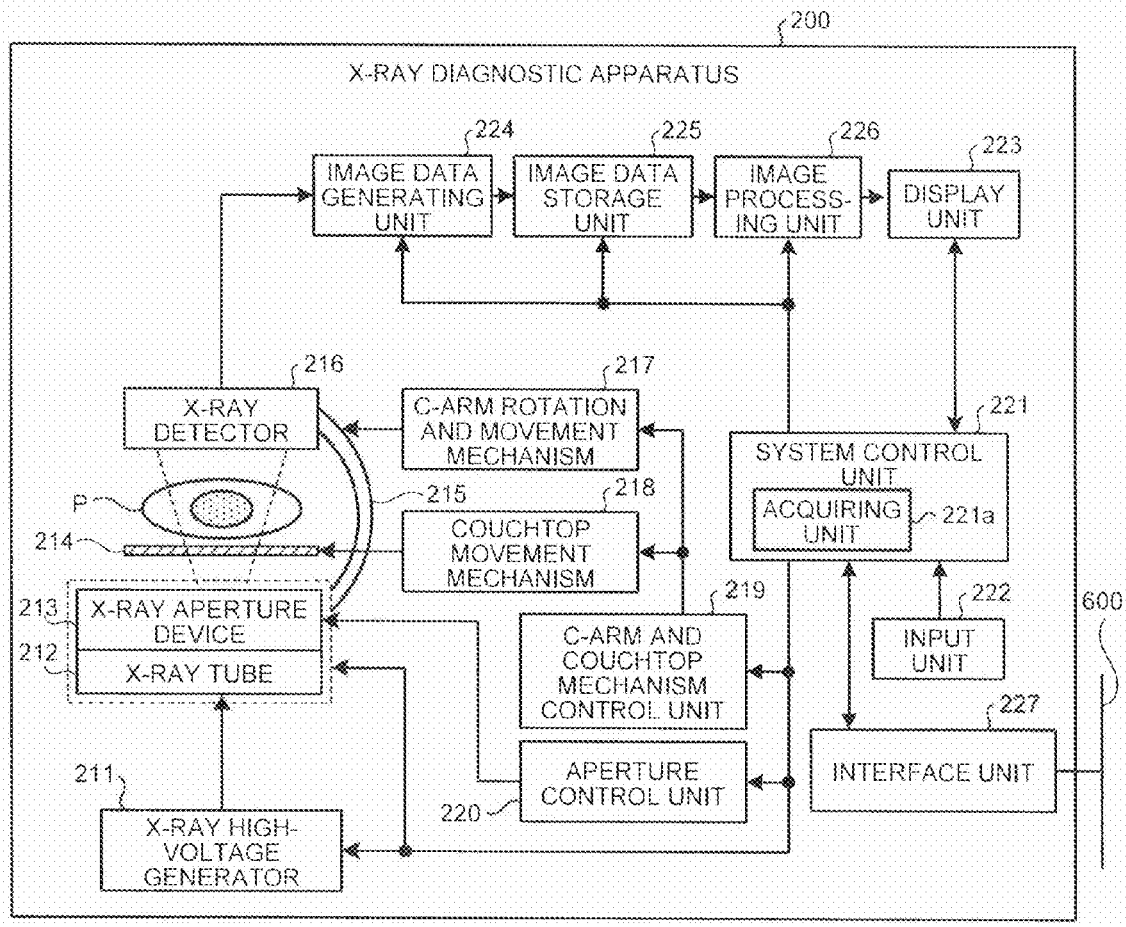
FIG. 8 is a block diagram of an exemplary configuration of an X-ray diagnostic apparatus according to the first embodiment.

The following describes an exemplary configuration of the X-ray diagnostic apparatus 200 illustrated in FIG. 1 with reference to FIG. 8. FIG. 8 is a block diagram of an exemplary configuration of the X-ray diagnostic apparatus according to the first embodiment. As illustrated in FIG. 8, the X-ray diagnostic apparatus 200 according to the first embodiment includes an X-ray high-voltage generator 211, an X-ray tube 212, an X-ray aperture device 213, a couchtop 214, a C-arm 215, and an X-ray detector 216. The X-ray diagnostic apparatus 200 according to the first embodiment further includes a C-arm rotation and movement mechanism 217, a couchtop movement mechanism 218, a C-arm and couchtop mechanism control unit 219, an aperture control unit 220, a system control unit 221, an input unit 222, and a display unit 223. The X-ray diagnostic apparatus 200 according to the first embodiment further includes an image data generating unit 224, an image data storage unit 225, and an image processing unit 226.

The X-ray high-voltage generator 211 generates a high voltage and supplies the high voltage thus generated to the X-ray tube 212 under the control of the system control unit 221. The X-ray tube 212 uses the high voltage supplied from the X-ray high-voltage generator 211, thereby generating an X-ray.

The X-ray aperture device 213 limits the X-ray generated by the X-ray tube 212 such that a region of interest of the subject P is selectively irradiated with the X-ray under the control of the aperture control unit 220. The X-ray aperture device 213 includes four slidable aperture blades, for example. Under the control of the aperture control unit 220, the X-ray aperture device 213 slides the aperture blades to limit the X-ray generated by the X-ray tube 212, thereby irradiating the subject P with the X-ray. The couchtop 214 is a bed on which the subject P is placed and is arranged on a couch, which is not illustrated.

The X-ray detector 216 detects an X-ray transmitting through the subject P. The X-ray detector 216 includes detection elements arrayed in a matrix, for example. The detection elements each convert the X-ray transmitting through the subject P into an electrical signal, accumulate the electrical signal, and transmit the electrical signal thus accumulated to the image data generating unit 224.

The C-arm 215 holds the X-ray tube 212, the X-ray aperture device 213, and the X-ray detector 216. The X-ray tube 212 and the X-ray aperture device 213 are arranged in a manner facing the X-ray detector 216 with the subject P interposed therebetween by the C-arm 215.

The C-arm rotation and movement mechanism 217 is a mechanism that rotates and moves the C-arm 215. The couchtop movement mechanism 218 is a mechanism that moves the couchtop 214. The C-arm and couchtop mechanism control unit 219 controls the C-arm rotation and movement mechanism 217 and the couchtop movement mechanism 218 under the control of the system control unit 221, thereby adjusting rotation and movement of the C-arm 215 and movement of the couchtop 214. The aperture control unit 220 adjusts the degree of opening of the aperture blades included in the X-ray aperture device 213 under the control of the system control unit 221, thereby controlling the irradiation range of the X-ray with which the subject P is irradiated.

The image data generating unit 224 uses the electrical signal converted from the X-ray by the X-ray detector 216, thereby generating X-ray image data. The image data generating unit 224 then stores the X-ray image data thus generated in the image data storage unit 225. The image data generating unit 224, for example, performs current/voltage conversion, analog/digital (A/D) conversion, and parallel/serial conversion on the electrical signal received from the X-ray detector 216, thereby generating X-ray image data.

The image data storage unit 225 stores therein image data generated by the image data generating unit 224. The image processing unit 226 performs various types of image processing on the image data stored in the image data storage unit 225. The image processing performed by the image processing unit 226 will be described later in detail.

The input unit 222 receives various types of instructions issued from an operator, such as a doctor and a technician, who operates the X-ray diagnostic apparatus 200. The input unit 222 includes a mouse, a keyboard, a button, a trackball, and a joystick, for example. The input unit 222 transfers the instructions received from the operator to the system control unit 221.

The display unit 223 displays a GUI that receives an instruction from the operator and the image data stored in the image data storage unit 225, for example. The display unit 223 includes a monitor, for example. The display unit 223 may include a plurality of monitors.

The system control unit 221 controls the entire operation of the X-ray diagnostic apparatus 200. The system control unit 221, for example, controls the X-ray high-voltage generator 211 based on an instruction from the operator transferred from the input unit 222, thereby adjusting the voltage supplied to the X-ray tube 212. Thus, the system control unit 221 controls the amount of the X-ray with which the subject P is irradiated and ON/OFF of irradiation of the X-ray. The system control unit 221, for example, controls the C-arm and couchtop mechanism control unit 219 based on an instruction from the operator, thereby adjusting rotation and movement of the C-arm 215 and movement of the couchtop 214. The system control unit 221, for example, controls the aperture control unit 220 based on an instruction from the operator, thereby adjusting the degree of opening of the aperture blades included in the X-ray aperture device 213. Thus, the system control unit 221 controls the irradiation range of the X-ray with which the subject P is irradiated.

The system control unit 221 controls the image data generation processing performed by the image data generating unit 224, the image processing performed by the image processing unit 226, and other processing based on an instruction from the operator. The system control unit 221 performs control such that the monitor of the display unit 223 displays the GUI that receives an instruction from the operator and displays the image data stored in the image data storage unit 225, for example.

To perform the various types of processing using output data received from the ultrasonic diagnostic apparatus 100, the system control unit 221 includes an acquiring unit 221a as illustrated in FIG. 3. The acquiring unit 221a is a processing unit that performs alignment, which will be described later, for example. In other words, assuming that the aligning unit 156b corresponds to a first aligning unit, the image processing system 1 includes the acquiring unit 221a corresponding to a second aligning unit. The processing performed by the acquiring unit 221a will be described later in detail.

An interface unit 227 is an interface provided for the in-hospital LAN 600, the ultrasonic diagnostic apparatus 200, the X-ray CT apparatus 300, the image storage device 400, and the image processing apparatus 500. The interface unit 227 according to the present embodiment, for example, receives output data output from the ultrasonic diagnostic apparatus 100 and transfers the output data thus received to the acquiring unit 221a included in the system control unit 221.

The explanation has been made of the entire configuration of the image processing system 1 according to the first embodiment. With this configuration, the image processing system 1 according to the first embodiment specifies an area requiring treatment by ultrasonography using the ultrasonic diagnostic apparatus 100. Specifically, an asynchronous area into which an electrode of a pacemaker is to be placed is specified from the three-dimensional analysis image data generated by the analyzing unit 156a in cardiac resynchronization therapy (CRT). In the CRT, the doctor places the electrode into a vein closest to the asynchronous area while referring to an X-ray image fluoroscopically captured by the X-ray diagnostic apparatus 200. Because the endocardial surface and the epicardial surface of the heart wall are hard to distinguish under X-ray fluoroscopic guidance, it is difficult to align X-ray image data with analysis image data, that is, X-ray image data with ultrasound image data.

Figure 9:
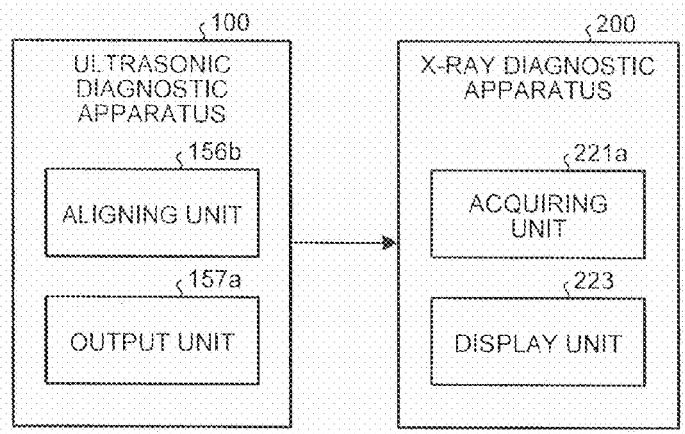
FIG. 9 is a diagram of processing units that carry out an image processing method performed by the image processing system according to the first embodiment.

To identify an area specified in the ultrasonic diagnosis under X-ray fluoroscopic guidance, the units illustrated in FIG. 9 perform the following processing in the first embodiment. FIG. 9 is a diagram of processing units that carry out an image processing method performed by the image processing system according to the first embodiment.

In the first embodiment, the aligning unit 156b serving as the first aligning unit included in the ultrasonic diagnostic apparatus 100 aligns first three-dimensional medical image data with second three-dimensional medical image data, the first three-dimensional medical image data and the second three-dimensional medical image data being obtained by capturing a certain tissue of a subject P. The first three-dimensional medical image data is three-dimensional medical image data in which motion of the certain tissue is analyzed. Specifically, the first three-dimensional medical image data is three-dimensional ultrasound image data. The second three-dimensional medical image data is three-dimensional medical image data visualizing a specific tissue identifiable in X-ray image data. In other words, the aligning unit 156b serving as the first aligning unit aligns three-dimensional ultrasound image data obtained by capturing the certain tissue of the subject P with second three-dimensional medial image data, the second three-dimensional medical image data being three-dimensional medical image data obtained by capturing the certain tissue of the subject P, being a three-dimensional medical image data visualizing a specific tissue that is identifiable in X-ray image data, and being different from the three-dimensional ultrasound image data. The certain tissue corresponds to the heart. Specifically, the second three-dimensional medical image data corresponds to three-dimensional X-ray CT image data or three-dimensional MRI image data. The second three-dimensional medical image data is three-dimensional contrast enhanced image data, for example, and is three-dimensional X-ray CT image data in which the coronary artery and the coronary vein are imaged or three-dimensional MRI image data in which the coronary artery and the coronary vein are imaged. The specific tissue described above is an identifiable tissue in X-ray image data. Specifically, the specific tissue described above is an identifiable tissue in X-ray contrast enhanced image data obtained by contrast enhanced radiography of the heart serving as the certain tissue. The specific tissue is the coronary artery or the coronary vein, for example. The second three-dimensional medical image data visualizing the specific tissue may be three-dimensional MRI image data in which a bloodstream is labeled by non-contrast radiography besides three-dimensional contrast enhanced image data, for example. The following describes the case where the second three-dimensional medical image data is three-dimensional contrast enhanced image data.

Because the enhancement of a coronary artery is higher than that of a coronary vein, three-dimensional X-ray CT image data in which the coronary artery is enhanced or three-dimensional MRI image data in which the coronary artery is enhanced are preferably used as the three-dimensional contrast enhanced image data. The following describes the case where three-dimensional X-ray CT image data in which the coronary artery serving as the specific tissue is enhanced is used as the three-dimensional contrast enhanced image data serving as the second three-dimensional medical image data.

The output unit 157a included in the ultrasonic diagnostic apparatus 100 outputs, as output data, data obtained by adding alignment information to the first three-dimensional medical image data (three-dimensional ultrasound image data) and to the second three-dimensional medical image data (three-dimensional contrast enhanced image data). Alternatively, the output unit 157a outputs synthetic data obtained by aligning and synthesizing the first three-dimensional medical image data (three-dimensional ultrasound image data) with the second three-dimensional medical image data (three-dimensional contrast enhanced image data) as output data.

The acquiring unit 221a serving as the second aligning unit included in the X-ray diagnostic apparatus 200 receives the output data. The acquiring unit 221a then aligns the second three-dimensional medical image data with one or a plurality of pieces of X-ray image data, the X-ray image data being obtained by capturing the certain tissue of the subject P in one or a plurality of capturing directions, and corresponding to the respective capturing directions. Alternatively, the acquiring unit 221a serving as the second aligning unit aligns the second three-dimensional medical image data with a piece of X-ray image data obtained by capturing the certain tissue of the subject P in a capturing direction and corresponding to the capturing direction. The display unit 223 included in the X-ray diagnostic apparatus 200 displays image data obtained by aligning the first three-dimensional medical image data with the X-ray image data of the certain tissue based on an alignment result of the aligning unit 156b serving as the first aligning unit and the alignment result of the acquiring unit 221a serving as the second aligning unit.

Specifically, the acquiring unit 221a acquires three-dimensional position information of the specific tissue in a three-dimensional capturing space of the X-ray image data based on an alignment result of the second three-dimensional medical image data with the one or the plurality of pieces of X-ray image data. Alternatively, the acquiring unit 221a acquires three-dimensional position information of the specific tissue in the three-dimensional capturing space of a piece of X-ray image data based on the alignment result of the second three-dimensional medical image data and the piece of X-ray image data.

More specifically, under the control of the acquiring unit 221a, the display unit 223 displays a projection image obtained by projecting the specific tissue on the one or the plurality of pieces of X-ray image data when the second three-dimensional medical image data is arranged in the three-dimensional capturing space of the X-ray diagnostic apparatus 200. The acquiring unit 221a then acquires the three-dimensional position information based on an operation for associating a position of the projection image with a position corresponding to the specific tissue in the one or the plurality of pieces of X-ray image data performed by an operator who refers to the display unit 223. Alternatively, under the control of the acquiring unit 221a, the display unit 223 displays a projection image obtained by projecting the specific tissue on a piece of X-ray image data when the second three-dimensional medical image data is arranged in the three-dimensional capturing space of the X-ray diagnostic apparatus 200. The acquiring unit 221a then acquires the three-dimensional position information based on an operation for associating the position of the projection image with the position corresponding to the specific tissue in the piece of X-ray image data performed by the operator who refers to the display unit 223.

In other words, the acquiring unit 221a performs the alignment by associating the "two-dimensional specific tissue depicted in the two-dimensional X-ray image data" with the "two-dimensional specific tissue obtained by projecting the three-dimensional specific tissue depicted in the second three-dimensional medical image data in the capturing direction of the X-ray image data" at three or more points. This enables the acquiring unit 221a serving as the second aligning unit to perform the alignment using a piece of X-ray image data obtained by capturing the specific tissue in a capturing direction.

The display unit 223 displays image data obtained by aligning the first three-dimensional medical image data or analysis image data generated by analyzing the first three-dimensional medical image data with the X-ray image data of the certain tissue, based on the three-dimensional position information of the specific tissue and based on a relative positional relation between the first three-dimensional medical image data and the second three-dimensional medical image data.

The one or the plurality of pieces of X-ray image data on which alignment is performed by the acquiring unit 221a serving as the second aligning unit are one or a plurality of pieces of X-ray contrast enhanced image data obtained by contrast enhanced radiography of the certain tissue. Alternatively, the one or the plurality of pieces of X-ray image data on which alignment is performed by the acquiring unit 221a serving as the second aligning unit are one or a plurality of pieces of X-ray image data obtained by capturing the specific tissue into which an instrument is inserted". The instrument described above is a guide wire inserted into the coronary artery or the coronary vein, for example. Because the guide wire is radiopaque, X-ray image data captured when the guide wire is inserted depicts a region corresponding to the coronary artery or the coronary vein clearly without injecting a contrast medium.

The following describes the case where the acquiring unit 221a performs alignment using "a plurality of pieces of X-ray contrast enhanced image data obtained by contrast enhanced radiography in a plurality of capturing directions" as the "plurality of pieces of X-ray image data". The contents described below are also applicable to the case where the "plurality of pieces of X-ray image data" correspond to "a plurality of pieces of X-ray image data captured in a plurality of capturing directions when the guide wire is inserted". Still alternatively, the contents described below are also applicable to the case where "a piece of X-ray image data obtained by contrast enhanced radiography in a capturing direction" or "a piece of X-ray image data captured in a capturing direction when the guide wire is inserted" is used as "a piece of X-ray image data".

The acquiring unit 221a, for example, receives output data and aligns three-dimensional contrast enhanced image data with a plurality of pieces of X-ray contrast enhanced image data obtained by capturing the heart of the subject P in a plurality of directions. Thus, the acquiring unit 221a acquires the three-dimensional position information of the specific tissue in the three-dimensional capturing space of the plurality of pieces of X-ray contrast enhanced image data.

Based on the three-dimensional position information of the specific tissue and the relative positional relation between the three-dimensional ultrasound image data and the three-dimensional contrast enhanced image data, the display unit 223, for example, displays image data obtained by aligning the analysis image data (three-dimensional analysis image data) with the X-ray image data of the certain tissue.

Figure 10:
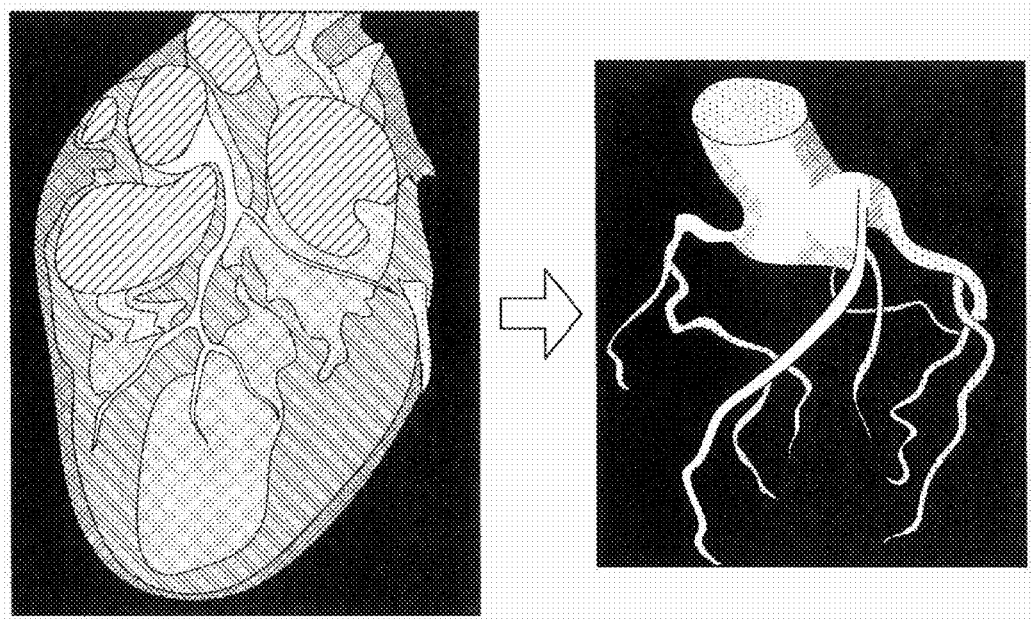
FIG. 10 and FIG. 11 are views for explaining an example of processing performed by the ultrasonic diagnostic apparatus according to the first embodiment.
Figure 11:
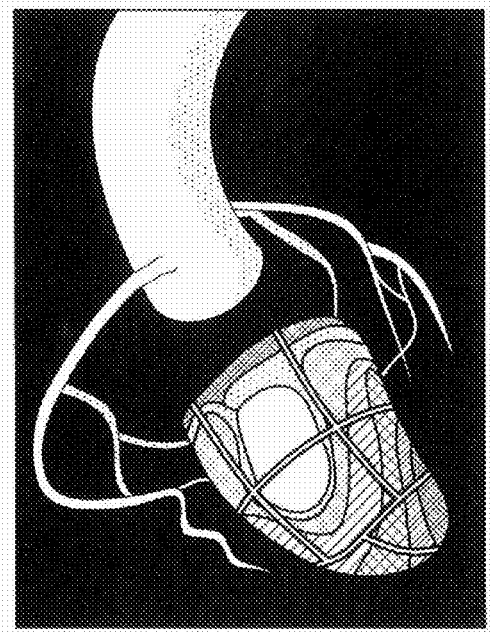

The following describes an example of the processing performed by the units illustrated in FIG. 9. FIG. 10 and FIG. 11 are views for explaining an example of the processing performed by the ultrasonic diagnostic apparatus according to the first embodiment.

As described above, the aligning unit 156b can align three-dimensional contrast enhanced region data segmented from three-dimensional contrast enhanced image data with three-dimensional analysis image data using the position detecting system formed of the position sensor 160 and the transmitter 161. In the present embodiment, for example, the aligning unit 156b performs the alignment on three-dimensional end-diastolic analysis image data (refer to FIG. 6) among a three-dimensional analysis image data group generated from the three-dimensional ultrasound image data group.

The aligning unit 156b performs the alignment on three-dimensional contrast enhanced region data (refer to the right figure in FIG. 10) obtained by extracting the coronary artery from the three-dimensional X-ray CT image data (refer to the left figure in FIG. 10) by performing threshold processing of the voxel value or a region expansion method. In the case where a time-series three-dimensional X-ray CT image data group is acquired, the aligning unit 156b performs the alignment on three-dimensional contrast enhanced region data obtained by extracting the coronary artery from the three-dimensional end-diastolic analysis image data. The present embodiment may also use three-dimensional contrast enhanced region data segmented by the X-ray CT apparatus 300 and the image processing apparatus 500, for example.

In the first embodiment, the aligning unit 156b may perform the alignment without using the position detecting system. The aligning unit 156b, for example, adjusts the position and the angles of the three axes in the three-dimensional space so as to align projection images obtained by projecting three-dimensional ultrasound image data at a predetermined time phase in a plurality of viewpoint directions with respective projection images obtained by projecting three-dimensional X-ray CT image data at the predetermined time phase in a plurality of viewpoint directions. Thus, the aligning unit 156b aligns the three-dimensional ultrasound image data with the three-dimensional X-ray CT image data at the same time phase. With this processing, the aligning unit 156b can align the three-dimensional analysis data with the three-dimensional contrast enhanced region data at the same time phase.

The output unit 157a outputs, as output data, data obtained by adding "alignment information" to the analysis image data that is an analysis result of the three-dimensional ultrasound image data" and to the second three-dimensional medical image data. The second three-dimensional medical image data may be "three-dimensional visualized region image data" obtained by extracting the "visualized specific tissue" from the second three-dimensional medical image data. Specifically, the output unit 157a transmits the three-dimensional analysis data and the three-dimensional contrast enhanced region data at the same time phase and the alignment information to the acquiring unit 221a as the output data. The acquiring unit 221a uses the alignment information, thereby arranging the three-dimensional analysis data and the three-dimensional contrast enhanced region data in the three-dimensional space in a manner aligned with each other as illustrated in FIG. 11.

Alternatively, the output unit 157a outputs, as output data, synthetic data obtained by aligning and synthesizing the analysis image data with the second three-dimensional medical image data. The second three-dimensional medical image data may be three-dimensional visualized region image data obtained by extracting the "visualized specific tissue" from the second three-dimensional medical image data. Specifically, the output unit 157a outputs synthetic data obtained by aligning and synthesizing the three-dimensional analysis data with the three-dimensional contrast enhanced region data at the same phase as output data. The synthetic data is data illustrated in FIG. 11. The output unit 157a configures, when outputting the synthetic data as the output data, the synthetic data having specific information being capable of switching of display and non-display of the "three-dimensional ultrasound image data (three-dimensional analysis data)" serving as the first three-dimensional medical image data and the three-dimensional contrast enhanced image data (three-dimensional contrast enhanced region data) serving as the second three-dimensional medical image data and the specific information being separable.

Specifically, the "three-dimensional contrast enhanced image data (three-dimensional contrast enhanced region data)" of the synthetic data is used for processing performed by the acquiring unit 221a. The "three-dimensional ultrasound image data (three-dimensional analysis data)" is eventually displayed by the display unit 223. Thus, it is preferable that display and non-display of these two pieces of data be switchable and that the pieces of data be separable. The output unit 157a uses the brightness value as the specific information, for example. The output unit 157a forms the three-dimensional analysis data as data represented by a brightness value of 511 gray-scale out of 512 gray-scale and forms the three-dimensional contrast enhanced region data as data represented by a brightness value of one gray-scale out of the 512 gray-scale, thereby generating the synthetic data.

The present embodiment may use the three-dimensional contrast enhanced image data as the output data. In this case, the image processing unit 226 included in the X-ray diagnostic apparatus 200 extracts the three-dimensional contrast enhanced region data from the three-dimensional contrast enhanced image data.

Figure 12:
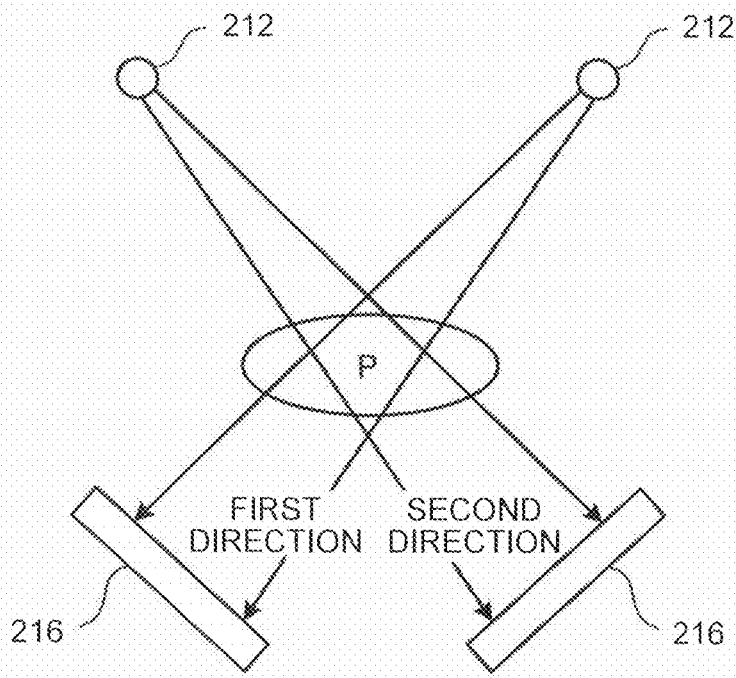

The acquiring unit 221a of the X-ray diagnostic apparatus 200 receives the output data. The acquiring unit 221a uses the output data, thereby aligning the X-ray contrast enhanced image data with the ultrasound image data. FIG. 12 and FIG. 13 are views for explaining an example of the processing performed by the X-ray diagnostic apparatus according to the first embodiment.

Under the control of the acquiring unit 221a, the X-ray diagnostic apparatus 200 performs contrast enhanced radiography on the heart of the subject P in a plurality of directions, thereby generating a plurality of pieces of X-ray contrast enhanced image data. Under the control of the acquiring unit 221a, the X-ray tube 212 irradiates the subject P with an X-ray in a first direction, and the X-ray detector 216 detects the X-ray passing through the subject P in the first direction as illustrated in FIG. 12, for example. Thus, the image data generating unit 224 generates X-ray contrast enhanced image data in the first direction. Furthermore, under the control of the acquiring unit 221a, the X-ray tube 212 irradiates the subject P with an X-ray in a second direction, and the X-ray detector 216 detects the X-ray passing through the subject P in the second direction as illustrated in FIG. 12, for example. Thus, the image data generating unit 224 generates X-ray contrast enhanced image data in the second direction.

The acquiring unit 221a uses the X-ray contrast enhanced image data in the first direction, the X-ray contrast enhanced image data in the second direction, and the output data, thereby acquiring the three-dimensional position information of the specific tissue. Because the specific tissue is the coronary artery, the X-ray contrast enhanced image data in the first direction and the X-ray contrast enhanced image data in the second direction are X-ray contrast enhanced image data at an arterial phase. If the specific tissue is the coronary vein, the X-ray image data in the first direction and the X-ray image data in the second direction are X-ray contrast enhanced image data at a venous phase.

As illustrated in FIG. 13, the acquiring unit 221a associates the coronary artery depicted in the three-dimensional contrast enhanced region data with the coronary arteries depicted in the respective pieces of X-ray contrast enhanced image data in the two directions. Thus, the acquiring unit 221a acquires the three-dimensional position information of the coronary artery in the three-dimensional contrast enhanced region data. The association is performed along the running path of the coronary artery at three or more points.

The acquiring unit 221a arranges the three-dimensional contrast enhanced region data in the three-dimensional capturing space of the X-ray diagnostic apparatus 200. The position at which the three-dimensional contrast enhanced region data is arranged is set by the operator, for example. Alternatively, the arrangement position is a preset position, for example. The acquiring unit 221a causes the image processing unit 226 to generate a projection image by projecting the specific tissue (coronary artery) in the three-dimensional contrast enhanced region data on a plurality of pieces of X-ray image data. Under the control of the acquiring unit 221a, the image processing unit 226 generates a projection image by projecting the three-dimensional contrast enhanced region data arranged in the three-dimensional capturing space in the first direction and the second direction, for example.

Under the control of the acquiring unit 221a, the display unit 223 displays the projection image obtained by projecting the three-dimensional contrast enhanced region data on the plurality of pieces of X-ray contrast enhanced image data. The acquiring unit 221a acquires the three-dimensional position information based on the operation for associating the position of the projection image with the position corresponding to the specific tissue in the plurality of pieces of X-ray contrast enhanced image data performed by the operator who refers to the display unit 223. The operator, for example, performs a moving operation (associating operation) such that the projection image of the coronary artery coincides with the coronary arteries viewed in the respective pieces of X-ray contrast enhanced image data.

The operator performs the moving operation such that the projection image substantially coincides with the coronary artery depicted in the X-ray image data. The acquiring unit 221a performs translation and rotation of the three-dimensional contrast enhanced region data arranged in the three-dimensional capturing space based on the amount of movement and the direction of movement of the projection image. The acquiring unit 221a then acquires the position of the three-dimensional contrast enhanced region data subjected to the processing as the three-dimensional position information. Based on the three-dimensional position information and the relative positional relation between the three-dimensional contrast enhanced region data and the three-dimensional analysis image data, the acquiring unit 221a rearranges the three-dimensional analysis image data in the three-dimensional capturing space. The moving operation may possibly expand, reduce, or deform the projection image. In this case, the three-dimensional contrast enhanced region data is expanded, reduced, or deformed in the three-dimensional capturing space. In this case, the three-dimensional analysis image data is expanded, reduced, or deformed after being rearranged in the three-dimensional capturing space by the acquiring unit 221a.

The image processing unit 226 projects the three-dimensional analysis image data rearranged in the three-dimensional capturing space based on the three-dimensional position information or the three-dimensional analysis image data rearranged in the three-dimensional capturing space based on the three-dimensional position information and then "expanded, reduced, or deformed" on the X-ray contrast enhanced image data of the heart of the subject P being captured in real time in a direction desired by the doctor. In other words, the image processing unit 226 generates image data by superimposing the projection image of the three-dimensional analysis image data aligned in the three-dimensional capturing space on the X-ray contrast enhanced image data of the heart. The direction desired by the doctor is a direction for capturing X-ray contrast enhanced image data suitable for placement of the electrode. The direction desired by the doctor can be arbitrarily changed during an operation. The image processing unit 226 projects the three-dimensional analysis image data on the X-ray contrast enhanced image data of the heart of the subject P being captured in real time in the direction thus changed.

Figure 14:
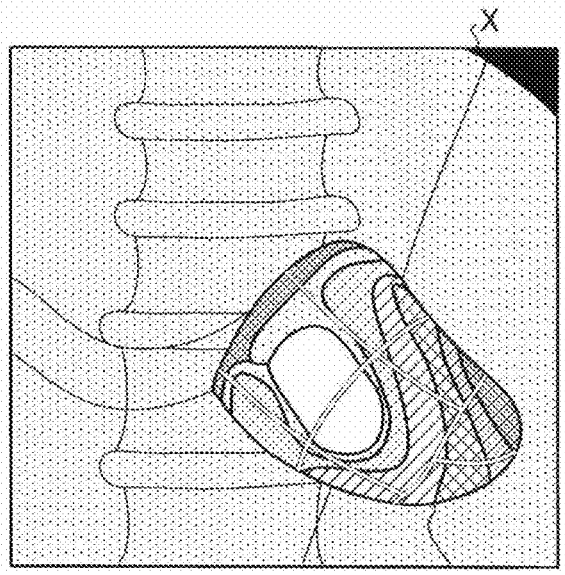
FIG. 14 is a view of an example of image data displayed in the first embodiment.

FIG. 14 is a view of an example of image data displayed in the first embodiment. By referring to image data X illustrated in FIG. 14, the doctor can place the electrode into a vein closest to the asynchronous area while checking the asynchronous area in the projection image of the three-dimensional analysis image data. Because the projection image of the three-dimensional analysis image data is a superimposed image, display and non-display thereof can be switched in response to a request from the operator. In the present embodiment, the projection target of the three-dimensional analysis image data to be superimposed on the X-ray image data may only be the asynchronous area. The opacity of the projection image of the three-dimensional analysis image data to be superimposed can be arbitrarily changed. The X-ray image data on which the projection image of the three-dimensional analysis image data aligned in the three-dimensional capturing space is superimposed is not limited to the X-ray contrast enhanced image data. The X-ray image data on which the projection image of the three-dimensional analysis image data aligned in the three-dimensional capturing space is superimposed may be X-ray image data captured in a direction desired by the doctor without injecting a contrast medium.

The first embodiment may output the output data including three-dimensional ultrasound image data serving as the first three-dimensional medical image data. In this case, the image data superimposed on the X-ray image data captured in the direction desired by the doctor is image data based on the three-dimensional ultrasound image data. The image data based on the three-dimensional ultrasound image data is ultrasound image data having a plurality of short-axis planes including a short-axis plane of the asynchronous area, for example.

Figure 15:
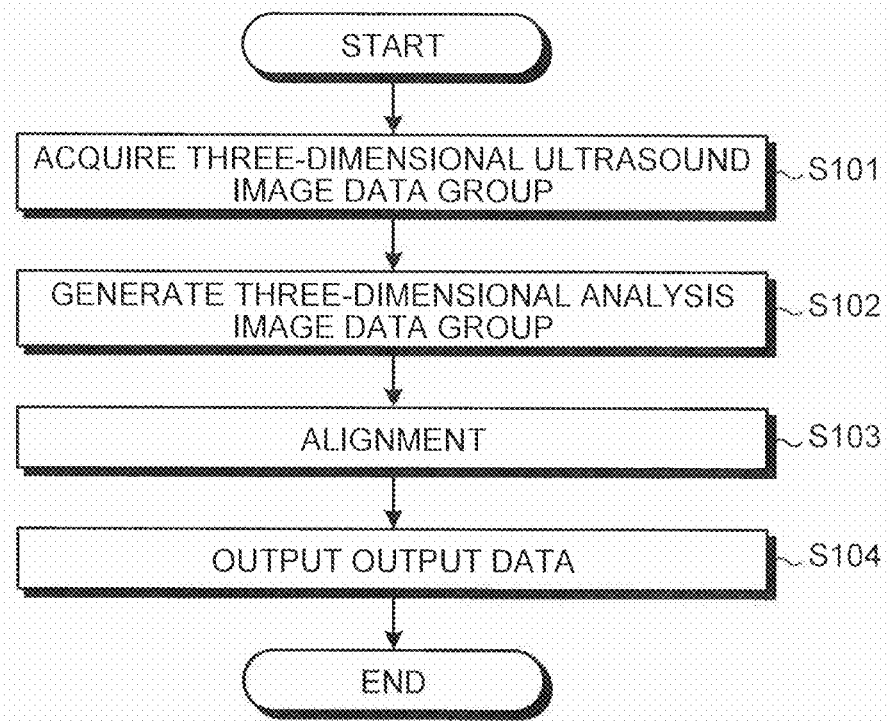
FIG. 15 is a flowchart for explaining an example of processing performed by the ultrasonic diagnostic apparatus according to the first embodiment.
Figure 16:
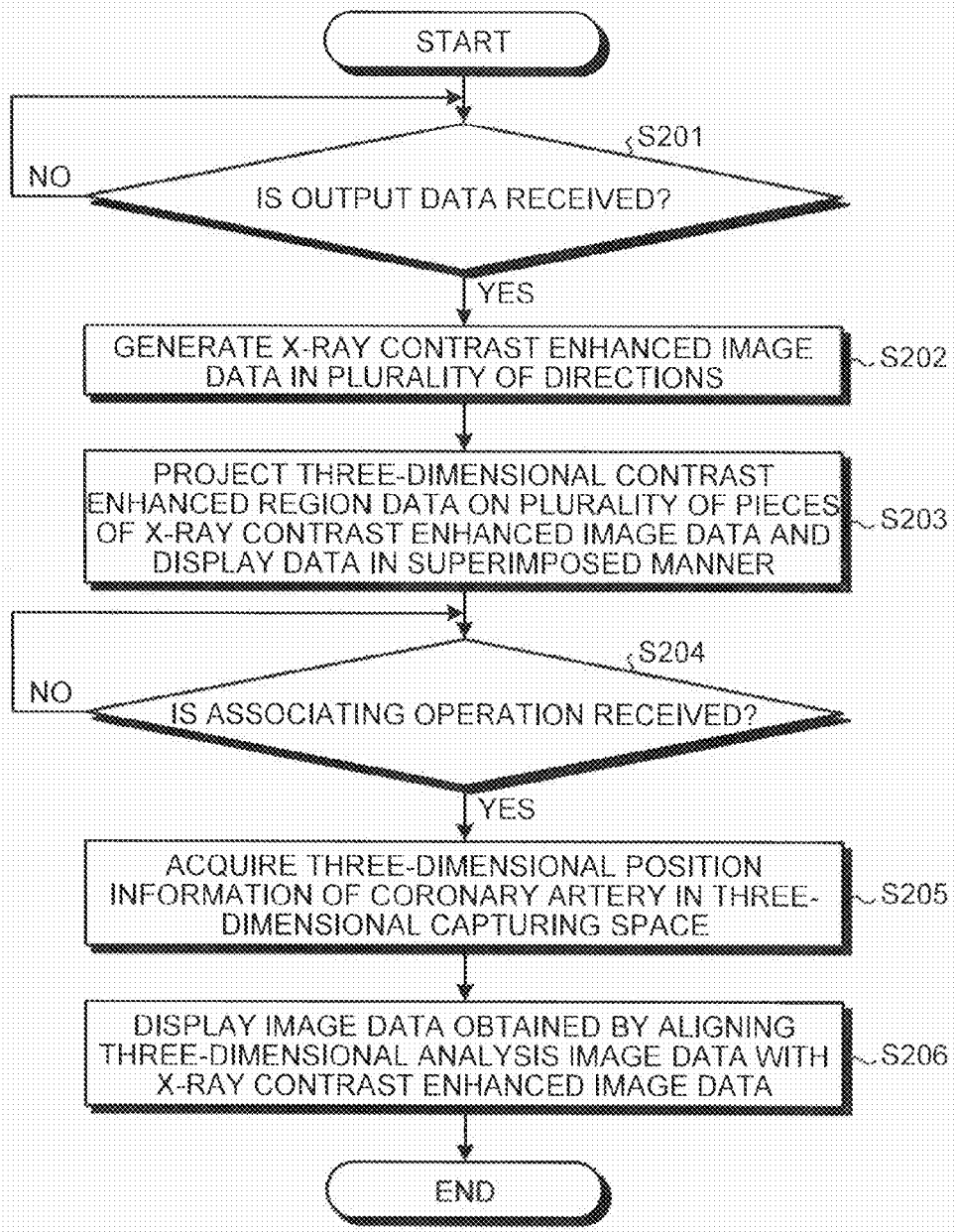
FIG. 16 is a flowchart for explaining an example of processing performed by the X-ray diagnostic apparatus according to the first embodiment.

The following describes a flow of the processing of the image processing system 1 according to the first embodiment with reference to FIG. 15 and FIG. 16. FIG. 15 is a flowchart for explaining an example of the processing performed by the ultrasonic diagnostic apparatus according to the first embodiment. FIG. 16 is a flowchart for explaining an example of the processing performed by the X-ray diagnostic apparatus according to the first embodiment. FIG. 15 illustrates an example of processing performed after initial alignment of the two-dimensional ultrasound image data and the three-dimensional X-ray CT image data is completed using a position detecting system.

As illustrated in FIG. 15, the ultrasonic diagnostic apparatus 100 according to the first embodiment acquires a three-dimensional ultrasound image data group of the heart (Step S101). The analyzing unit 156a generates a three-dimensional analysis image data group (Step S102). The aligning unit 156b aligns three-dimensional analysis image data with three-dimensional contrast enhanced region data at the same time phase (Step S103).

The output unit 157a, for example, generates synthetic data by aligning and synthesizing the three-dimensional analysis image data with the three-dimensional contrast enhanced region data as output data and outputs the output data (Step S104). The processing is then terminated.

As illustrated in FIG. 16, the acquiring unit 221a included in the X-ray diagnostic apparatus 200 according to the first embodiment determines whether output data is received from the ultrasonic diagnostic apparatus 100 (Step S201). If no output data is received (No at Step S201), the acquiring unit 221a waits until output data is received.

By contrast, if output data is received (Yes at Step S201), the acquiring unit 221a controls each unit of the X-ray diagnostic apparatus 200 so as to generate a plurality of pieces of X-ray contrast enhanced image data in a plurality of directions (Step S202). Specifically, the X-ray diagnostic apparatus 200 captures the heart of the subject P at the arterial phase in a plurality of directions.

Under the control of the acquiring unit 221a, the display unit 223 projects the three-dimensional contrast enhanced region data on the plurality of pieces of X-ray contrast enhanced image data, thereby displaying the data in a superimposed manner (Step S203). The acquiring unit 221a determines whether an associating operation for associating the projection image with the coronary artery in the plurality of pieces of X-ray contrast enhanced image data is received from the operator (Step S204). If no associating operation is received (No at Step S204), the acquiring unit 221a waits until an associating operation is received.

By contrast, if an associating operation is received (Yes at Step S204), the acquiring unit 221a acquires the three-dimensional position information of the coronary artery in the three-dimensional capturing space based on the associating operation (Step S205). Under the control of the acquiring unit 221a, the display unit 223 displays image data obtained by aligning the three-dimensional analysis image data with the X-ray contrast enhanced image data (Step S206). The processing is then terminated.

As described above, the first embodiment aligns the three-dimensional ultrasound image data with the two-dimensional X-ray image data with the three-dimensional X-ray CT image data (or the three-dimensional MRI image data) intervening therebetween. Specifically, the first embodiment can identify, in the three-dimensional X-ray CT image data, an area corresponding to a scanning area in the three-dimensional ultrasound imaged data with the position detecting system provided with the position sensor 160. Furthermore, the first embodiment can align a plurality of pieces of volume data at a voxel level based on tissue information depicted in the two areas.

As a result, the first embodiment can facilitate alignment of the three-dimensional analysis image data based on the ultrasound image data with the three-dimensional contrast enhanced region data. Because a coronary artery has a characteristic form, the first embodiment can further facilitate alignment of the three-dimensional contrast enhanced region data at the arterial phase with the X-ray contrast enhanced image data at the arterial phase. In other words, the first embodiment can align the ultrasound image data (three-dimensional analysis image data) with the X-ray contrast enhanced image data. Thus, the first embodiment makes it possible to identify the area specified in the ultrasonic diagnosis under X-ray fluoroscopic guidance. In the first embodiment, the doctor can place the electrode near the asynchronous area while referring to the projection image of the three-dimensional analysis image data that can be displayed in a superimposed manner by the alignment.

Second Embodiment

Figure 17:
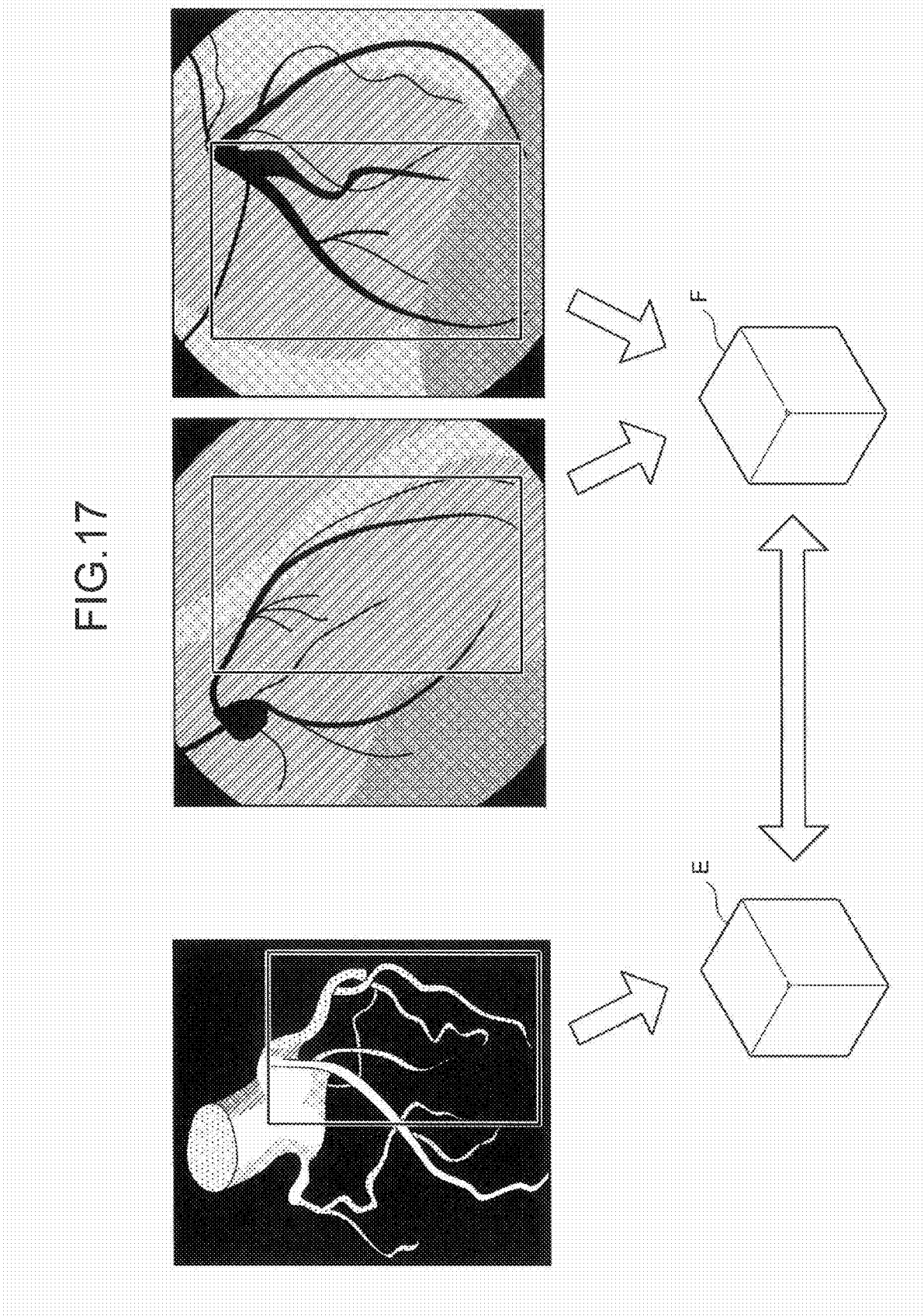
FIG. 17 is a view for explaining a second embodiment.

The first embodiment describes the case where the three-dimensional position information is acquired based on an operation performed by the operator. A second embodiment will describe the case where three-dimensional position information is automatically acquired with no operation performed by the operator with reference to FIG. 17. FIG. 17 is a view for explaining the second embodiment.

An image processing system 1 according to the second embodiment has the same configuration as that of the image processing system 1 according to the first embodiment explained with reference to FIG. 1. When performing the alignment on the plurality of pieces of the X-ray image data captured in a plurality of capturing directions, an acquiring unit 221a serving as a second aligning unit according to the second embodiment aligns the second three-dimensional medical image data with three-dimensional X-ray image data reconstructed from the plurality of pieces of X-ray image data by performing pattern matching between a plurality of pieces of three-dimensional image data. The acquiring unit 221a according to the second embodiment, for example, aligns three-dimensional contrast enhanced image data with three-dimensional X-ray contrast enhanced image data reconstructed from a plurality of pieces of X-ray contrast enhanced image data by performing pattern matching between a plurality of pieces of three-dimensional image data. Examples of the pattern matching include processing using cross-correlation, autocorrelation, mutual information, standardized mutual information, and the correlation ratio.

In the case where data included in output data is three-dimensional contrast enhanced region data extracted from the three-dimensional contrast enhanced image data, the target of the pattern matching is the three-dimensional contrast enhanced region data. Under the control of the acquiring unit 221a, for example, an image processing unit 226 back-projects the plurality of pieces of X-ray contrast enhanced image data captured in a plurality of directions in the three-dimensional capturing space, thereby reconstructing the three-dimensional X-ray contrast enhanced image data. In the second embodiment, the three-dimensional X-ray contrast enhanced image data is reconstructed from a plurality of pieces of X-ray contrast enhanced image data captured in two directions, three directions, or 50 directions.

To reduce the load in the pattern matching, the following processing is preferably performed, for example. The acquiring unit 221a serving as the second aligning unit aligns a three-dimensional region of interest set in the second three-dimensional medical image data with a three-dimensional region of interest set in the three-dimensional X-ray image data. The acquiring unit 221a, for example, aligns the three-dimensional region of interest set in the three-dimensional contrast enhanced image data (or the three-dimensional contrast enhanced region data) with the three-dimensional region of interest set in the three-dimensional X-ray contrast enhanced image data.

As illustrated in FIG. 17, for example, the operator sets a three-dimensional region of interest (ROI) in the three-dimensional contrast enhanced region data. As a result, the image processing unit 226 extracts "volume data E", which is three-dimensional contrast enhanced region data of the three-dimensional ROI, for example. Furthermore, the operator sets a two-dimensional ROI in two pieces of X-ray contrast enhanced image data as illustrated in FIG. 17, thereby setting a three-dimensional ROI. As a result, the image processing unit 226 reconstructs "volume data F", which is three-dimensional X-ray contrast enhanced image data of the three-dimensional ROI. These three-dimensional ROI may be automatically set by the acquiring unit 221a based on the brightness.

The acquiring unit 221a performs pattern matching between the volume data E and the volume data F, thereby performing alignment therebetween. Thus, the acquiring unit 221a acquires the three-dimensional position information of the specific tissue (e.g., the coronary artery). The processing described above may be performed on three-dimensional X-ray image data reconstructed from a plurality of pieces of X-ray image data captured in a plurality of directions when a guide wire is inserted, for example. Because the subsequent processing is the same as that described in the first embodiment, the explanation thereof will be omitted.

The following describes a flow of the processing of the image processing system 1 according to the second embodiment with reference to FIG. 18. FIG. 18 is a flowchart for explaining an example of processing performed by an X-ray diagnostic apparatus according to the second embodiment. Because processing performed by an ultrasonic diagnostic apparatus 100 according to the second embodiment is the same as that described in the first embodiment, the explanation thereof will be omitted.

As illustrated in FIG. 18, the acquiring unit 221a included in an X-ray diagnostic apparatus 200 according to the second embodiment determines whether output data is received from the ultrasonic diagnostic apparatus 100 (Step S301). If no output data is received (No at Step S301), the acquiring unit 221a waits until output data is received.

By contrast, if output data is received (Yes at Step S301), the acquiring unit 221a controls each unit of the X-ray diagnostic apparatus 200 so as to generate a plurality of pieces of X-ray contrast enhanced image data in a plurality of directions (Step S302). Specifically, the X-ray diagnostic apparatus 200 captures the heart of the subject P at the arterial phase in a plurality of directions.

The acquiring unit 221a receives setting of a three-dimensional ROI (Step S303). The acquiring unit 221a extracts three-dimensional contrast enhanced region data of the three-dimensional ROI and reconstructs three-dimensional X-ray contrast enhanced image data of the three-dimensional ROI from the plurality of pieces of X-ray contrast enhanced image data (Step S304). The acquiring unit 221a performs pattern matching between the three-dimensional contrast enhanced region data of the three-dimensional ROI and the three-dimensional X-ray contrast enhanced image data of the three-dimensional ROI (Step S305).

The acquiring unit 221a acquires the three-dimensional position information of the coronary artery in the three-dimensional capturing space (Step S306). Under the control of the acquiring unit 221a, a display unit 223 displays image data obtained by aligning the three-dimensional analysis image data with the X-ray contrast enhanced image data (Step S307). The processing is then terminated.

As described above, the second embodiment can automatically acquire the three-dimensional position information of the specific tissue. Thus, the second embodiment can further facilitate alignment of the ultrasound image data (three-dimensional analysis image data) with the X-ray contrast enhanced image data.

The processing of each unit described in the first and the second embodiments may be performed by the X-ray CT apparatus 300 and the image processing apparatus 500. A part or all of the generation of the analysis image data, the alignment of the ultrasound image data with the X-ray CT image data, the output of the output data, and the acquisition of the three-dimensional position information of the specific tissue may be performed by the X-ray CT apparatus 300 and the image processing apparatus 500, for example. The superimposed image of the analysis image data and the X-ray image data thus aligned may be generated by the X-ray CT apparatus 300 and the image processing apparatus 500. In other words, a specific aspect of distribution and integration of processing units described in the first and the second embodiments is not limited to that illustrated in the drawings. All or a part of the processing units may be functionally or physically distributed and integrated in arbitrary units depending on various types of loads and usage.

The first and the second embodiments describe the case where the first three-dimensional medical image data is three-dimensional ultrasound image data and the second three-dimensional medical image data is three-dimensional X-ray computed tomography (CT) image data or three-dimensional magnetic resonance imaging (MRI) image data, visualizing the specific tissue. The contents described in the first and the second embodiments are applicable to any case as long as the first three-dimensional medical image data is three-dimensional medical image data in which motion of the certain tissue can be analyzed and the second three-dimensional medical image data is three-dimensional medical image data visualizing the specific tissue. The contents described in the first and the second embodiments, for example, are applicable to the case where the first three-dimensional medical image data is three-dimensional MRI image data captured at a time phase when the contrast of the myocardium is enhanced and the second three-dimensional medical image data is three-dimensional X-ray CT image data captured at a time phase when the contrast of the coronary artery or the coronary vein is enhanced. Alternatively, the contents described in the first and the second embodiments, for example, are applicable to the case where the first three-dimensional medical image data is three-dimensional X-ray CT image data captured at a time phase when the contrast of the myocardium is enhanced and the second three-dimensional medical image data is three-dimensional X-ray CT image data captured at a time phase when the contrast of the coronary vein is enhanced.

The image processing method described in the first and the second embodiments can be performed by a computer, such as a personal computer and a workstation, executing an image processing program prepared in advance. The image processing program may be distributed over a network such as the Internet. Furthermore, the image processing program may be recorded in a computer-readable recording medium, such as a hard disk, a flexible disk (FD), a compact disc read-only memory (CD-ROM), a magneto-optical disk (MO), and a digital versatile disk (DVD), and executed by a computer reading the image processing program from the recording medium.

As described above, the first and the second embodiments can identify an area specified in an ultrasonic diagnosis under X-ray fluoroscopic guidance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system comprising:
first aligning circuitry that aligns first three-dimensional medical image data with second three-dimensional medical image data, the first three-dimensional medical image data and the second three-dimensional medical image data being obtained by capturing a certain tissue of a subject;
output circuitry that outputs, as output data,
data obtained by adding alignment information to the first three-dimensional medical image data and to the second three-dimensional medical image data, or
synthetic data obtained by aligning and synthesizing the first three-dimensional medical image data with the second three-dimensional medical image data;
second aligning circuitry that receives the output data and aligns the second three-dimensional medical image data with one or a plurality of pieces of X-ray image data, the X-ray image data being obtained by capturing the certain tissue of the subject in one or a plurality of capturing directions, and corresponding to the respective capturing directions; and
a display that displays image data obtained by aligning the first three-dimensional medical image data with the X-ray image data of the certain tissue based on an alignment result of the first aligning circuitry and the second aligning circuitry,
wherein
the first three-dimensional medical image data is three-dimensional medical image data in which motion of the certain tissue is analyzable;
the second three-dimensional medical image data is three-dimensional medical image data visualizing a specific tissue identifiable in X-ray image data;
the one or the plurality of pieces of X-ray image data on which alignment is performed by the second aligning circuitry are one or a plurality of pieces of X-ray contrast enhanced image data obtained by contrast enhanced radiography of the certain tissue or one or a plurality of pieces of X-ray image data obtained by capturing the specific tissue into which an instrument is inserted;
the second aligning circuitry acquires three-dimensional position information of the specific tissue in a three-dimensional capturing space of the X-ray image data based on an alignment result of the second three-dimensional medical image data with the one or the plurality of pieces of X-ray image data; and
the display displays image data obtained by aligning
the first three-dimensional medical image data or analysis image data generated by analyzing the first three-dimensional medical image data with the X-ray image data of the certain tissue, based on the three-dimensional position information of the specific tissue and based on a relative positional relation between the first three-dimensional medical image data and the second three-dimensional medical image data.

2. The image processing system according to claim 1, wherein
the display displays a projection image obtained by projecting the specific tissue on the one or the plurality of pieces of X-ray image data when the second three-dimensional medical image data is arranged in the three-dimensional capturing space, and
the second aligning circuitry acquires the three-dimensional position information based on an operation for associating a position of the projection image with a position corresponding to the specific tissue in the one or the plurality of pieces of X-ray image data performed by an operator who refers to the display.

3. The image processing system according to claim 1, wherein, when performing the alignment on the plurality of pieces of the X-ray image data, the second aligning circuitry aligns the second three-dimensional medical image data with three-dimensional X-ray image data reconstructed from the plurality of pieces of X-ray image data by performing pattern matching between a plurality of pieces of three-dimensional image data.

4. The image processing system according to claim 3, wherein the second aligning circuitry aligns a three-dimensional region of interest set in the second three-dimensional medical image data with a three-dimensional region of interest set in the three-dimensional X-ray image data.

5. The image processing system according to claim 1, wherein, the output circuitry configures, when outputting the synthetic data as the output data, the synthetic data as data having specific information
being capable of switching of display and non-display of the first three-dimensional medical image data and the second three-dimensional medical image data, and
being separable.

6. The image processing system according to claim 1, wherein the output circuitry outputs, as the output data,
data obtained by adding alignment information to analysis image data that is an analysis result of the first three-dimensional medical image data and to the second three-dimensional medical image data, or
synthetic data obtained by aligning and synthesizing the analysis image data with the second three-dimensional medical image data.

7. The image processing system according to claim 1, wherein the first three-dimensional medical image data is three-dimensional ultrasound image data and the second three-dimensional medical image data is three-dimensional X-ray computed tomography (CT) image data or three-dimensional magnetic resonance imaging (MRI) image data.

8. An X-ray diagnostic apparatus comprising:
second aligning circuitry that receives, as output data obtained based on an alignment result of first aligning circuitry,
data obtained by adding alignment information to first three-dimensional medical image data and to second three-dimensional medical image data, the first three-dimensional medical image data and the second three-dimensional medical image data obtained by capturing a certain tissue of a subject, or
synthetic data obtained by aligning and synthesizing the first three-dimensional medical image data with the second three-dimensional medical image data,
and that aligns the second three-dimensional medical image data with one or a plurality of pieces of X-ray image data obtained by capturing the certain tissue of the subject in one or a plurality of capturing directions, the X-ray image data corresponding to the respective capturing directions; and
a display that displays image data obtained by aligning the first three-dimensional medical image data with X-ray image data of the certain tissue, based on an alignment result of the first aligning circuitry and the second aligning circuitry, wherein
the first three-dimensional medical image data is three-dimensional medical image data in which motion of the certain tissue is analyzable;
the second three-dimensional medical image data is three-dimensional medical image data visualizing a specific tissue identifiable in X-ray image data;
the one or the plurality of pieces of X-ray image data on which alignment is performed by the second aligning circuitry are one or a plurality of pieces of X-ray contrast enhanced image data obtained by contrast enhanced radiography of the certain tissue or one or a plurality of pieces of X-ray image data obtained by capturing the specific tissue into which an instrument is inserted;
the second aligning circuitry acquires three-dimensional position information of the specific tissue in a three-dimensional capturing space of the X-ray image data based on an alignment result of the second three-dimensional medical image data with the one or the plurality of pieces of X-ray image data; and
the display displays image data obtained by aligning the first three-dimensional medical image data or analysis image data generated by analyzing the first three-dimensional medical image data with the X-ray image data of the certain tissue, based on the three-dimensional position information of the specific tissue and based on a relative positional relation between the first three-dimensional medical image data and the second three-dimensional medical image data.

9. An image processing method comprising:
aligning, by first aligning circuitry, first three-dimensional medical image data with second three-dimensional medical image data, the first three-dimensional medical image data and the second three-dimensional medical image data being obtained by capturing a certain tissue of a subject;
outputting, by output circuitry, as output data,
data obtained by adding alignment information to the first three-dimensional medical image data and to the second three-dimensional medical image data, or
synthetic data obtained by aligning and synthesizing the first three-dimensional medical image data with the second three-dimensional medical image data;
receiving, by second aligning circuitry, the output data and aligning, by the second aligning circuitry, the second three-dimensional medical image data with one or a plurality of pieces of X-ray image data obtained by capturing the certain tissue of the subject in one or a plurality of capturing directions, the X-ray image data corresponding to the respective capturing directions; and
displaying, by a display, image data obtained by aligning the first three-dimensional medical image data with the X-ray image data of the certain tissue based on an alignment result of the first aligning circuitry and the second aligning circuitry, wherein
the first three-dimensional medical image data is three-dimensional medical image data in which motion of the certain tissue is analyzable;

the second three-dimensional medical image data is three-dimensional medical image data visualizing a specific tissue identifiable in X-ray image data;

the one or the plurality of pieces of X-ray image data on which alignment is performed by the second aligning circuitry are one or a plurality of pieces of X-ray contrast enhanced image data obtained by contrast enhanced radiography of the certain tissue or one or a plurality of pieces of X-ray image data obtained by capturing the specific tissue into which an instrument is inserted;

the second aligning circuitry acquires three-dimensional position information of the specific tissue in a three-dimensional capturing space of the X-ray image data based on an alignment result of the second three-dimensional medical image data with the one or the plurality of pieces of X-ray image data; and the display displays image data obtained by aligning the first three-dimensional medical image data or analysis image data generated by analyzing the first three-dimensional medical image data with the X-ray image data of the certain tissue, based on the three-dimensional position information of the specific tissue and based on a relative positional relation between the first three-dimensional medical image data and the second three-dimensional medical image data.

10. An image processing system comprising:
first aligning circuitry that aligns first three-dimensional medical image data with second three-dimensional medical image data, the first three-dimensional medical image data and the second three-dimensional medical image data being obtained by capturing a certain tissue of a subject;
output circuitry that outputs, as output data, data obtained by adding alignment information to the first three-dimensional medical image data and to the second three-dimensional medical image data;
second aligning circuitry that receives the output data and aligns the second three-dimensional medical image data with one or a plurality of pieces of X-ray image data, the X-ray image data being obtained by capturing the certain tissue of the subject in one or a plurality of capturing directions, and corresponding to the respective capturing directions; and
a display that displays image data obtained by aligning the first three-dimensional medical image data with the X-ray image data of the certain tissue based on an alignment result of the first aligning circuitry and the second aligning circuitry.

11. The image processing system according to claim 10, wherein the first three-dimensional medical image data is three-dimensional medical image data in which motion of the certain tissue is analyzable and the second three-dimensional medical image data is three-dimensional medical image data visualizing a specific tissue identifiable in X-ray image data.

12. The image processing system according to claim 11, wherein the one or the plurality of pieces of X-ray image data on which alignment is performed by the second aligning circuitry are
one or a plurality of pieces of X-ray contrast enhanced image data obtained by contrast enhanced radiography of the certain tissue or
one or a plurality of pieces of X-ray image data obtained by capturing the specific tissue into which an instrument is inserted.

13. The image processing system according to claim 12, wherein
the second aligning circuitry acquires three-dimensional position information of the specific tissue in a three-dimensional capturing space of the X-ray image data based on an alignment result of the second three-dimensional medical image data with the one or the plurality of pieces of X-ray image data, and
the display displays image data obtained by aligning
the first three-dimensional medical image data or analysis image data generated by analyzing the first three-dimensional medical image data with
the X-ray image data of the certain tissue, based on the three-dimensional position information of the specific tissue and based on a relative positional relation between the first three-dimensional medical image data and the second three-dimensional medical image data.

14. The image processing system according to claim 13, wherein
the display displays a projection image obtained by projecting the specific tissue on the one or the plurality of pieces of X-ray image data when the second three-dimensional medical image data is arranged in the three-dimensional capturing space, and
the second aligning circuitry acquires the three-dimensional position information based on an operation for associating a position of the projection image with a position corresponding to the specific tissue in the one or the plurality of pieces of X-ray image data performed by an operator who refers to the display.

15. The image processing system according to claim 13, wherein, when performing the alignment on the plurality of pieces of the X-ray image data, the second aligning circuitry aligns the second three-dimensional medical image data with three-dimensional X-ray image data reconstructed from the plurality of pieces of X-ray image data by performing pattern matching between a plurality of pieces of three-dimensional image data.

16. The image processing system according to claim 15, wherein the second aligning circuitry aligns a three-dimensional region of interest set in the second three-dimensional medical image data with a three-dimensional region of interest set in the three-dimensional X-ray image data.

17. The image processing system according to claim 10, wherein the output circuitry outputs, as the output data,
data obtained by adding alignment information to analysis image data that is an analysis result of the first three-dimensional medical image data and to the second three-dimensional medical image data, or
synthetic data obtained by aligning and synthesizing the analysis image data with the second three-dimensional medical image data.

18. The image processing system according to claim 10, wherein the first three-dimensional medical image data is three-dimensional ultrasound image data and the second three-dimensional medical image data is three-dimensional X-ray computed tomography (CT) image data or three-dimensional magnetic resonance imaging (MRI) image data.

19. An X-ray diagnostic apparatus comprising:
second aligning circuitry that receives, as output data obtained based on an alignment result of first aligning circuitry,
data obtained by adding alignment information to first three-dimensional medical image data and to second three-dimensional medical image data, the first three-dimensional medical image data and the second three-dimensional medical image data obtained by capturing a certain tissue of a subject, and that aligns the second three-dimensional medical image data with one or a plurality of pieces of X-ray image data obtained by capturing the certain tissue of the subject in one or a plurality of capturing directions, the X-ray image data corresponding to the respective capturing directions; and a display that displays image data obtained by aligning the first three-dimensional medical image data with X-ray image data of the certain tissue, based on an alignment result of the first aligning circuitry and the second aligning circuitry.

20. An image processing method comprising:

aligning, by first aligning circuitry, first three-dimensional medical image data with second three-dimensional medical image data, the first three-dimensional medical image data and the second three-dimensional medical image data being obtained by capturing a certain tissue of a subject;

outputting, by output circuitry, as output data, data obtained by adding alignment information to the first three-dimensional medical image data and to the second three-dimensional medical image data;

receiving, by second aligning circuitry, the output data and aligning, by the second aligning circuitry, the second three-dimensional medical image data with one or a plurality of pieces of X-ray image data obtained by capturing the certain tissue of the subject in one or a plurality of capturing directions, the X-ray image data corresponding to the respective capturing directions; and displaying, by a display, image data obtained by aligning the first three-dimensional medical image data with the X-ray image data of the certain tissue based on an alignment result of the first aligning circuitry and the second aligning circuitry.

* * * * *